United States Patent
Edge

(12) 
(10) Patent No.: US 6,673,604 B1
(45) Date of Patent: Jan. 6, 2004

(54) MUSCLE CELLS AND THEIR USE IN CARDIAC REPAIR

(75) Inventor: Albert Edge, Cambridge, MA (US)

(73) Assignee: Diacrin, Inc., Charlestown, MA (US)

( * ) Notice: Subject to any disclaimer, the term of this patent is extended or adjusted under 35 U.S.C. 154(b) by 0 days.

(21) Appl. No.: 09/624,885

(22) Filed: Jul. 24, 2000

Related U.S. Application Data
(60) Provisional application No. 60/145,849, filed on Jul. 23, 1999.

(51) Int. Cl.[7] .............................. C12N 5/06; C12N 5/08
(52) U.S. Cl. ........................ 435/347; 435/325; 435/371
(58) Field of Search ................................ 435/325, 347, 435/371; 424/93.21

(56) References Cited

U.S. PATENT DOCUMENTS

| | | |
|---|---|---|
| 5,130,141 A | 7/1992 | Law et al. |
| 5,143,842 A | 9/1992 | Ham et al. |
| 5,199,942 A | 4/1993 | Gillis |
| 5,324,656 A | 6/1994 | Ham et al. |
| 5,374,544 A | 12/1994 | Schwartz et al. |
| 5,405,772 A | 4/1995 | Ponting |
| 5,538,722 A | 7/1996 | Blau et al. |
| 5,543,318 A | 8/1996 | Smith et al. |
| 5,580,779 A | 12/1996 | Smith et al. |
| 5,602,301 A | 2/1997 | Field |
| 5,733,727 A | 3/1998 | Field |
| 5,968,983 A | 10/1999 | Kaesemeyer |
| 5,972,013 A | 10/1999 | Schmidt |
| 5,985,653 A | 11/1999 | Armstrong et al. |
| 5,994,129 A | 11/1999 | Armstrong et al. |
| 6,015,671 A | 1/2000 | Field |
| 6,096,532 A | 8/2000 | Armstrong et al. |
| 6,099,832 A | 8/2000 | Mickle et al. |
| 6,107,034 A * | 8/2000 | Wiegel et al. |
| 6,110,459 A | 8/2000 | Mickle et al. |
| 6,228,635 B1 | 5/2001 | Armstrong et al. |
| 6,238,908 B1 | 5/2001 | Armstrong et al. |
| 6,239,172 B1 | 5/2001 | Kaesemeyer |
| 6,261,832 B1 | 7/2001 | Law |

FOREIGN PATENT DOCUMENTS

| | | |
|---|---|---|
| EP | 898967 | 3/1999 |
| WO | WO 90/15863 | 12/1990 |
| WO | WO 9512979 | 5/1995 |
| WO | WO 95/14079 | 5/1995 |
| WO | WO 96/18303 | 6/1996 |
| WO | WO 9638543 | 12/1996 |
| WO | WO 9817784 | 4/1998 |
| WO | WO 9827995 | 7/1998 |
| WO | WO 9854301 | 12/1998 |
| WO | WO 9966036 | 12/1999 |
| WO | WO 00/78119 | 12/2000 |

OTHER PUBLICATIONS

Allen et al. (1991) (J. Cell Physiology 149:525–535).*
Ansari, et al., An Investigation of Human Response to Perennial Ryegrass (Lolium Perenne) Pollen Cytochrome c (Lol p X). *J. Allergy Clin. Immunol.* 80: 229–235, 1987.
Atkins, et al., "Myogenic Cell Transplantation Improves in Vivo Regional Performance in Infarcted Rabbit Myocardium", *J. Heart Lung Transplant,* 18(2): 1173–1180, 1999.
Atkins, et al., "Intracardiac Transplantation of Skeletal Myoblasts Yields Two Populations of Striated Cells in Situ", *Ann. Thorac Surg.* 67(1): 124–129, 1999.
Gussoni, et al., "Normal Dystrophin Transcripts Detected in Duchenne Muscular Dystrophy Pateints After Myoblast Transplantation" *Nature,* 356:435–438, 1992.
Hagege, et al., "Regeneration of the Myocardium: A New Role in the Treatment of Ischemic Heart Disease?", *Hypertension,* 38(6): 1413–1415, 2001.
Li, et al., "Human Pediatric and Adult Ventricular Cardiomyocytes in Culture: Assessment of Phenotypic Changes with Passaging" *Cardiovascular Res.,* 32:362–373, 1996.
Menasche, et al., "Autologous Skeletal Myoblast Transplantation for Cardiac Insufficiency. First Clinic Case", *Arch. Mal. Coeur. Vaiss.* 94(3): 180–182, 2001.
Pouzet, et al., Transplantation of Autologous Skeletal Myoblasts in Ischemic Cardiac Insufficiency, *J. Soc. Biol.,* 195(1): 47–49, 2001.
Suzuki, et al., "Intracoronary Infusion of Skeletal Myoblasts Improves Cardiac Function in Doxorubicin–Induced Heart Failure", *Circulation,* 104(12 Suppl): I213–I217, 2001.
Suzuki, et al., "Cell Transplantation for the Treatment of Acute Myocardial Infarction Using Vascular Endothelial Growth Factor–Expressing Skeletal Myoblasts," *Circulation,* 104(12 Supp): I207–I212, 2001.
Van Meter, et al., "Myoblast Transplantation in the Porcine Model: A Potential Technique for Myocardial Repair", *J. Thorac Cardiovasc Surg.* 110(5):1442–1448, 1995.
Thompson, et al., "Fetal Transplants Show Promise" *Science,* 257:868–870, 1992.

(List continued on next page.)

Primary Examiner—Christina Chan
Assistant Examiner—F. Pierre VanderVegt
(74) Attorney, Agent, or Firm—Choate, Hall & Stewart; Brenda Herschbach Jarrell

(57) ABSTRACT

Muscle cells and methods for using the muscle cells are provided. In one embodiment, the invention provides transplantable skeletal muscle cell compositions and their methods of use. In one embodiment, the muscle cells can be transplanted into patients having disorders characterized by insufficient cardiac function, e.g., congestive heart failure, in a subject by administering the skeletal myoblasts to the subject. The muscle cells can be autologous, allogeneic, or xenogeneic to the recipient.

5 Claims, 7 Drawing Sheets

(3 of 7 Drawing Sheet(s) Filed in Color)

OTHER PUBLICATIONS

Watanabe, et al., "Cardiomyocyte Transplantation in a Porcine Myocardial Infarction Model," *Cell Transplant,* 7(3):239–246, 1998.

Foster R F et al. "Laminin Selectively Promotes The Replication And Differentiation Of Myblasts" Journal Of Cell Biology 1987, 105 (4 part 2):288A.

Grepin C, et al. "Enhanced cardiogenesis in embryonic stem cells overexpressing the GATA–4 transcription factor". *Development 1997 Jun*;124(12):2387–95.

Chiu, R. C.J. et al., "Cellular cardiomyoplasty: myocardial regeneration with satellite cell implantation," *Ann. Thorac. Surg.,* 1995 Jul;60(1):12–18.

Gold, H.K. et al., "Cellular therapy for myocardial repair: Successful transplantation of human myoblasts by intracoronary injection into the canine heart after acute myocardial infarction," *Abstracts from the 70th Scientific Sessions,* 3170, p. I–567.

Kao, R.L. et al., "Satellite cells for myocardial regeneration," Abstract, *Cardiac Muscle Physiology,* 1989; 32:220.

Kao, R.L. et al., "Regeneration of injured myocardium from implanted satellite cells," Abstract, *Circulation Supp. II,* 1991; 84(4):II–386.

Klug, M.G. et al., "Genetically selected cardiomyocytes from differentiating embronic stem cells form stable intracardiac grafts," *J. Clin. Invest.,* 1996 Jul 1:98(1):216–24.

Koh, G.Y. et al., "Differentiation and long–term survival of C2C12 myoblast grafts in heart," *J. Clin. Invest.,* 1993 Sep;92(3):1548–54.

Koh, G.Y. et al., "Targeted expression of transforming growth factor–beta 1 in intracardiac grafts promotes vascular endothelial cell DNA synthesis," *J. Clin. Invest.,* 1995 Jan;95(1):114–21.

Leor, J. et al., "Transplantation of fetal myocardial tissue into the infarcted myocardium of rat. A potential method for repair of infarcted myocardium?" *Circulation,* 1996 Nov;94(9 Suppl):II332–336.

Leor, J. et al., "Gene transfer and cell transplant: an experimental approach to repair a 'broken heart'," *Cardiovasc. Res.,* 1997 Sep;35(3):431–441.

Li, R.–K. et al., "In vivo survival and function of transplanted rat cardiomyocytes," *Cir. Res.,* 1996 Feb;78(2):283–288.

Li, R.–K. et al., "Cardiomyocyte transplantation improves heart function," *Ann. Thorac. Surg.,* 1996 Sep;62(3):654–61.

Li, R.–K. et al., "Human pediatric and adult ventricular cardiomyocytes in culture: assessment of phenotypic changes with passaging," *Cardiovasc. Res.,* 1996 Aug;32(2):362–373.

Li, R.–K. et al., "Natural history of fetal rat cardiomyocytes transplanted into adult rat myocardial scar tissue," *Circulation,* 1997 Nov 4;96(9 Suppl):II–179–87.

Li, R.–K. et al., "Cell therapy to repair broken hearts," *Can. J. Cardiol.,* 1998 May;14(5):735–44.

Li, R.–K. et al., "Effect of donor age contractility of transplanted rat cardiomyocytes," *J. Mol. Cell Cardiol.* 1994; 26:A162.

Li, R.–K. et al., "Method of culturing cardiomyocytes from human pediatric ventricular myocardium," *J. Tiss. Cult. Meth.* 1992; 14:93–100.

Magovern, G.J. et al., "Clinical cardiomyoplasty: review of the ten–year United States experience," *Ann. Thorac. Surg.,* 1996 Jan;61(1):413–419.

Mannion, J.D. et al., "Histochemical and fatigue characteristics of conditioned canine latissimus dorsi muscle," *Circ. Res.,* 1986 Feb;58(2):298–304.

Morrow, N. G. et al., "Increased expression of fibroblast growth factors in a rabbit skeletal muscle model of exercise conditioning," *J. Clin. Invest.,* 1990 Jun;85(6)1816–20.

Murry, C.E. et al., "Skeletal and cardiac myoblast transplantation after myocardial necrosis: Possible routes to muscle regeneration," *Circulation* Suppl. 1, Vol. 92(8) (1995).

Murry, C.E. et al., "Skeletal myoblast transplantation for repair of myocardial necrosis," *J. Clin. Invest.,* 1996 Dec 1;98(11):2512–23.

Neumeyer, A.M. et al., "Arterial delivery of myoblasts to skeletal muscle," *Neurology,* 1992 Dec;42(12):2258–62.

Robinson, S.W. et al., "Arterial delivery of genetically labelled skeletal myoblasts to the murine heart: long–term survival and phenotypic modification of implanted myoblasts," *Cell Transplant.,* 1996 Jan–Feb;5(1):77–91.

Schweitzer, J.S. et al., "Fibroblasts modulate expression of Thy–1 on the surface of skeletal myoblasts," *Exp. Cell Res.,* 1987 Sep;172(1):1–20.

Soonpaa, M.H. et al., "Potential approaches for myocardial regeneration," *Ann. N. Y. Acad. Sci.,* 1995 Mar 27;752:446–54.

Soonpaa, M.H. et al., "Formation of nascent intercalated disks between grafted fetal cardiomyocytes and host myocardium," *Science* 1994; 264:98–101.

Taylor, D.A. et al., "Delivery of primary autologous skeletal myoblasts into rabbit heart by coronary infusion: a potential approach to myocardial repair," *Proc. Assoc. Am. Physicians,* 1997 May;109(3):245–53.

Taylor, D.A. et al., "Regenerating functional myocardium: improved performance after skeletal myoblast transplantation," *Nat. Med.,* 1998 Aug;4(8):929–33.

Wang, J.–M. et al., "Persistent systemic production of human factor IX in mice by skeletal myoblast–mediated gene transfer: feasibility of repeat application to obtain therapeutic levels," *Blood,* 1997 Aug 1;90(3):1075–82.

Watanabe, E. et al., "Cardiomyocyte transplantaiton in a porcine myocardial infarction model," *Cell Transplant.,* 1998 May–Jun;7(3):239–46.

Yoon, P.D. et al., "Myocardial regeneration. Transplanting satellite cells into damaged myocardium," *Tex. Heart Inst. J.,* 1995;22(2):119–25.

\* cited by examiner

MUSCLE CELLS AND THEIR USE IN CARDIAC REPAIR

RELATED APPLICATIONS

This application claims priority to U.S. Provisional Application No. 60/145,849, filed on Jul. 23, 1999, incorporated herein in its entirety by this reference.

BACKGROUND OF THE INVENTION

Heart disease is the predominant cause of disability and death in all industrialized nations. Cardiac disease can lead to decreased quality of life and long term hospitalization. In addition, in the United States, it accounts for about 335 deaths per 100,000 individuals (approximately 40% of the total mortality) overshadowing cancer, which follows with 183 deaths per 100,000 individuals. Four categories of heart disease account for about 85–90% of all cardiac-related deaths. These categories are: ischemic heart disease, hypertensive heart disease and pulmonary hypertensive heart disease, valvular disease, and congenital heart disease. Ischemic heart disease, in its various forms, accounts for about 60–75% of all deaths caused by heart disease. In addition, the incidence of heart failure is increasing in the United States. One of the factors that renders ischemic heart disease so devastating is the inability of the cardiac muscle cells to divide and repopulate areas of ischemic heart damage. As a result, cardiac cell loss as a result of injury or disease is irreversible.

Human to human heart transplants have become the most effective form of therapy for severe heart damage. Many transplant centers now have one-year survival rates exceeding 80–90% and five-year survival rates above 70% after cardiac transplantation. Heart transplantation, however, is severely limited by the scarcity of suitable donor organs. In addition to the difficulty in obtaining donor organs, the expense of heart transplantation prohibits its widespread application. Another unsolved problem is graft rejection. Foreign hearts are poorly tolerated by the recipient and are rapidly destroyed by the immune system in the absence of immunosuppressive drugs. While immunosuppressive drugs may be used to prevent rejection, they also block desirable immune responses such as those against bacterial and viral infections, thereby placing the recipient at risk of infection. Infections, hypertension, and renal dysfunction caused by cyclosporin, rapidly progressive coronary atherosclerosis, and immunosuppressant-related cancers have been major complications however.

Cellular transplantation has been the focus of recent research into new means of repairing cardiac tissue after myocardial infarctions. A major problem with transplantation of adult cardiac myocytes is that they do not proliferate in culture. (Yoon et al. (1995) *Tex. Heart Inst. J.* 22:119). To overcome this problem, attention has focused on the possible use of skeletal myoblasts. Skeletal muscle tissue contains satellite cells which are capable of proliferation. However, methods of purifying and growing these cells are complicated. There is a clear need, therefore, to address the limitations of the current heart transplantation therapies in the treatment of heart disease.

SUMMARY OF THE INVENTION

To overcome the limitations of the current heart repair methodologies, the present invention provides isolated muscle cells. In a preferred embodiment, the invention pertains to skeletal myoblasts, compositions including the skeletal myoblasts, and methods for transplanting skeletal myoblasts into subjects. In addition, the invention pertains to cardiomyocytes, methods for inducing the proliferation of cardiomyocytes, and methods for transplanting cardiomyocytes to subjects. The present invention offers numerous advantages over the cells and methods of the prior art.

In one aspect, the invention provides a method for preparing a transplantable muscle cell composition comprising skeletal myoblast cells and fibroblast cells comprising culturing the composition on a surface coated with poly-L-lysine and laminin in a medium comprising EGF such that the transplantable composition is prepared. Preferably, the cells are permitted to double less than about 10 times in vitro prior to transplantation such that the fibroblast to myoblast ratio is approximately 1:2 to 1:1.

In one aspect, the invention provides a transplantable composition comprising skeletal myoblast cells and fibroblast cells and, in one embodiment, can comprise from about 20% to about 70% myoblasts and, preferably, about 40–60% myoblasts or about 50% myoblasts. In another embodiment, the transplantable composition comprises at least about 20%, 25%, 30%, 35%, 40%, 45%, 50%, 55%, 60%, 65%, 70%, 75%, 80%, 85%, 90%, 98% or 99% myoblasts.

The muscle cells of the invention may be cultured in vitro prior to transplantation and are preferably cultured on a surface coated with poly-L-lysine and laminin in a medium comprising EGF. Alternatively, the surface can be coated with collagen and the composition cultured in a medium comprising FGF.

The muscle cells of the invention preferably engraft into cardiac tissue after transplantation into a subject. The muscle cells of the invention can endogenously express an angiogenic factor, or can be administered in the form of a composition which comprises an angiogenic factor, or the muscle cells of the invention can be engineered to express an angiogenic gene product in order to induce angiogenesis in the recipient heart.

The invention also provides for modifying, masking, or eliminating an antigen on the surface of a cell in the composition such that upon transplantation of the composition into a subject lysis of the cell is inhibited. In one embodiment, PT85 or W6/32 is used to mask an antigen.

The invention further provides a method for treating a condition in a subject characterized by damage to cardiac tissue comprising transplanting a composition comprising skeletal myoblast cells and fibroblast cells into a subject such that the condition is thereby treated.

The invention further provides a method for treating myocardial ischemic damage comprising transplanting a composition comprising skeletal myoblast cells and, optionally, fibroblast cells into a subject such that the myocardial ischemic damage is thereby treated.

In one embodiment, skeletal myoblast cells of the invention can be induced to become more like cardiac cells. In a preferred embodiment, a cardiac cell phenotype in a skeletal myoblast is promoted by recombinantly expressing a cardiac cell gene product in the myoblast so that the cardiac cell phenotype is promoted. In one embodiment, the gene product is a GATA transcription factor and, preferably is GATA4 or GATA6.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A is a photograph of transplanted cells which were sorted prior to transplantation, while FIG. 1B is a photograph of transplanted cells which were not sorted and were only allowed to undergo several population doublings in vitro prior to transplantation.

FIGS. 2A (lower power) and 2B (higher power) shows staining of such a graft for factor VIII at three weeks post transplantation. Vessels can be seen in the center of the graft.

FIG. 5 is the infarcted left ventricular free wall of a rat under increasing magnification, with trichome staining (A, B, and C) and immunohistochemical staining for myogenin, a nuclear transcription factor unique to skeletal myoblasts (D, E, and F). The encircled area identifies the region of cell implantation. Arrows highlight two grafts within the infarct region.

FIG. 6 is the maximum exercise capacity determined prior to cell therapy (1 week post-MI), 3 weeks post-implantation, and 6 weeks post-implantation. Non-infarcted control animals, dashed bar; MI animals, dark bar; MI+ animals, light bar; *, $p<0.05$ vs. 0 weeks (pre-therapy); #, $p<0.05$ vs. MI.

FIG. 7 is the systolic pressure-volume relationships at three weeks post-cell therapy (A) and six weeks post-cell therapy (B). Control hearts, dashed line; MI hearts, dark boxes, MI+ hearts, light boxes, *, $p<0.05$ vs. control.

FIG. 8 is the diastolic pressure-volume relationships at three weeks post-cell therapy (A) and six weeks post-cell therapy (B). Control hearts, dashed line; MI hearts, dark boxes, MI+ hearts, light boxes, *, $p<0.05$ vs. control, #, $p<0.05$ vs. MI.

DETAILED DESCRIPTION OF THE INVENTION

Figure 1A:
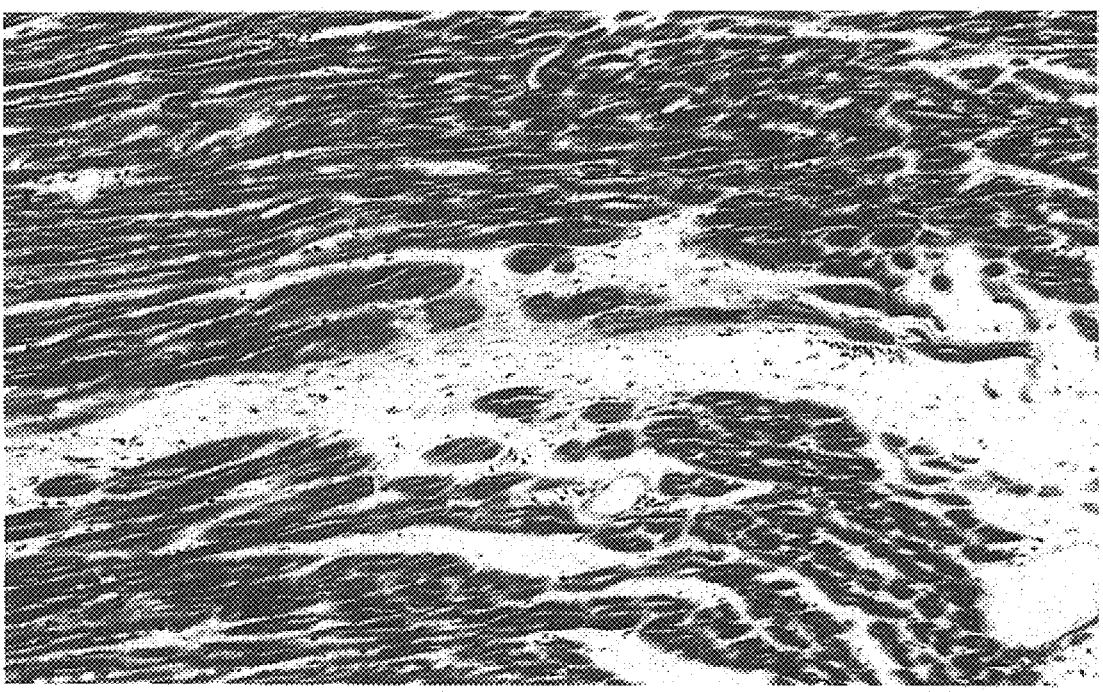
FIGS. 1A–1B shows that muscle cells that undergo fewer population doublings result in better survival after transplantation.

The invention features isolated muscle cells, e.g., skeletal myoblasts, cardiomyocytes, or compositions comprising skeletal myoblasts or cardiomyocytes and their methods of use. In one embodiment, the invention provides isolated skeletal myoblasts and populations of isolated skeletal myoblasts suitable for introduction into a recipient. The invention further provides methods of transplanting such cells. In addition, the invention provides methods of expanding adult cardiomyocytes, isolated cardiomyocytes, populations of isolated, expanded cardiomyocytes, compositions including cardiomyocytes, and methods for transplanting cardiomyocytes into a recipient. These cells can be transplanted, for example, into recipient subjects that have disorders such as ischemic heart disease, hypertensive heart disease and pulmonary hypertensive heart disease (cor pulmonale), valvular disease, congenital heart disease, dilated cardiomyopathy, hypertrophic cardiomyopathy, myocarditis, or any condition which leads to heart failure, e.g., which is characterized by insufficient cardiac function.

I. Definitions

For the sake of convenience, certain terms used throughout the specification are collected here.

As used herein, the term "isolated" refers to a cell which has been separated from its natural environment. This term includes gross physical separation of the cell from its natural environment, e.g., removal from the donor. Preferably "isolated" includes alteration of the cell's relationship with the neighboring cells with which it is in direct contact by, for example, dissociation. The term "isolated" does not refer to a cell which is in a tissue section, is cultured as part of a tissue section, or is transplanted in the form of a tissue section. When used to refer to a population muscle cells, the term "isolated" includes populations of cells which result from proliferation of the isolated cells of the invention.

The terms "skeletal myoblasts" and "skeletal myoblast cells" are used interchangeably herein and refer to a precursor of myotubes and skeletal muscle fibers. The term "skeletal myoblasts" also includes satellite cells, mononucleate cells found in close contact with muscle fibers in skeletal muscle. Satellite cells lie near the basal lamina of skeletal muscle myofibers and can differentiate into myofibers. The term "cardiomyocyte" includes a muscle cell which is derived from cardiac muscle. Such cells have one nucleus and are, when present in the heart, joined by intercalated disc structures. As used herein, the term "engrafts" includes the incorporation of transplanted muscle cells or muscle cell compositions of the invention into heart tissue with or without the direct attachment of the transplanted cell to a cell in the recipient heart, (e.g., by the formation desmosomes or gap junctions) such that the cells enhance cardiac function, e.g., by increasing cardiac output.

As used herein the term "angiogenesis" includes the formation of new capillary vessels in the heart tissue into which the muscle cells of the invention are transplanted. Preferably, the muscle cells of the invention, when transplanted into an ischemic zone, enhance angiogenesis. This angiogenesis can occur, e.g., as a result of the act of transplanting the cells, as a result of the secretion of angiogenic factors from the muscle cells, and/or as a result of the secretion of endogenous angiogenic factors from the heart tissue.

As used herein the phrase "more like cardiac cells" includes skeletal muscle cells which are made to more closely resemble cardiac muscle cells in phenotype. Such cardiac-like cells can be characterized, e.g., by a change in their physiology (e.g., they may have a slower twitch phenotype, a slower shortening velocity, use of oxidative phosphorylation for ATP production, expression of cardiac forms of contractile proteins, higher mitochondrial content, higher myoglobin content, and greater resistance to fatigue than skeletal muscle cells) and/or the production of molecules which are normally not produced by skeletal muscle cells or which are normally produced in low amounts by skeletal muscle cells (e.g., those proteins produced from genes encoding the myocardial contractile apparatus and the Ca++ ATPase associated with cardiac slow twitch, phospholamban, and/or β myosin heavy molecules).

As used herein the phrase "GATA transcription factor" includes members of the GATA family of zinc finger transcription factors. GATA transcription factors play important roles in the development of several mesodermally derived cell lineages. Preferably, GATA transcription factors include GATA-4 and/or GATA-6. The GATA-6 and GATA-4 proteins share high-level amino acid sequence identity over a proline-rich region at the amino terminus of the protein that is not conserved in other GATA family members.

As used herein, the term "antibody" is intended to include immunoglobulin molecules and immunologically active portions of immunoglobulin molecules, i.e., molecules that contain an antigen binding site which specifically binds (immunoreacts with) an antigen, such as Fab and F(ab')$_2$ fragments. The terms "monoclonal antibodies" and "monoclonal antibody composition", as used herein, refer to a population of antibody molecules that contain only one species of an antigen binding site capable of immunoreacting with a particular epitope of an antigen, whereas the term "polyclonal antibodies" and "polyclonal antibody composition" refer to a population of antibody molecules that contain multiple species of antigen binding sites capable of interacting with a particular antigen. A monoclonal antibody compositions thus typically display a single binding affinity for a particular antigen with which it immunoreacts.

As used herein, the phrase "cardiac damage" or "disorder characterized by insufficient cardiac function" includes an impairment or absence of a normal cardiac function or presence of an abnormal cardiac function. Abnormal cardiac function can be the result of disease, injury, and/or aging. As used herein, abnormal cardiac function includes morphological and/or functional abnormality of a cardiomyocyte or a population of cardiomyocytes. Non-limiting examples of morphological and functional abnormalities include physical deterioration and/or death of cardiomyocytes, abnormal growth patterns of cardiomyocytes, abnormalities in the physical connection between cardiomyocytes, under- or over-production of a substance or substances by cardiomyocytes, failure of cardiomyocytes to produce a substance or substances which they normally produce, and transmission of electrical impulses in abnormal patterns or at abnormal times. Abnormal cardiac function is seen with many disorders including, for example, ischemic heart disease, e.g., angina pectoris, myocardial infarction, chronic ischemic heart disease, hypertensive heart disease, pulmonary heart disease (cor pulmonale), valvular heart disease, e.g., rheumatic fever, mitral valve prolapse, calcification of mitral annulus, carcinoid heart disease, infective endocarditis, congenital heart disease, myocardial disease, e.g., myocarditis, dilated cardiomyopathy, hypertensive cardiomyopathy, cardiac disorders which result in congestive heart failure, and tumors of the heart, e.g., primary sarcomas and secondary tumors.

As used herein, the phrase "myocardial ischemia" includes a lack of oxygen flow to the heart which results in "myocardial ischemic damage." As used herein, the phrase "myocardial ischemic damage" includes damage caused by reduced blood flow to the myocardium. Non-limiting examples of causes of myocardial ischemia and myocardial ischemic damage include: decreased aortic diastolic pressure, increased intraventricular pressure and myocardial contraction, coronary artery stenosis (e.g., coronary ligation, fixed coronary stenosis, acute plaque change (e.g., rupture, hemorrhage), coronary artery thrombosis, vasoconstriction), aortic valve stenosis and regurgitation, and increased right atrial pressure. Non-limiting examples of adverse effects of myocardial ischemia and myocardial ischemic damage include: myocyte damage (e.g., myocyte cell loss, myocyte hypertrophy, myocyte cellular hyperplasia), angina (e.g., stable angina, variant angina, unstable angina, sudden cardiac death), myocardial infarction, and congestive heart failure.

The term "treating" as used herein includes reducing or alleviating at least one adverse effect or symptom of a disorder characterized by myocardial ischemia, myocardial ischemic damage, cardiac damage or insufficient cardiac function. Adverse effects or symptoms of cardiac disorders are numerous and well-characterized. Non-limiting examples of adverse effects or symptoms of cardiac disorders include: dyspnea, chest pain, palpitations, dizziness, syncope, edema, cyanosis, pallor, fatigue, and death. For additional examples of adverse effects or symptoms of a wide variety of cardiac disorders, see Robbins, S. L. et al. (1984) Pathological Basis of Disease (W. B. Saunders Company, Philadelphia) 547–609; Schroeder, S. A. et al. eds. (1992) Current Medical Diagnosis & Treatment (Appleton & Lange, Connecticut) 257–356.

II. Muscle Cells of the Invention

Cells that can be transplanted using the instant methods include skeletal myoblasts and cardiomyocytes. The cells used in this invention can be derived from a suitable mammalian source, e.g., from pigs or from humans. They can be, for example, autologous, allogeneic, or xenogeneic to the subject into which they are transplanted. In preferred embodiments, the cells are human cells and are used for transplantation into the same individual from which they were derived or are used for transplantation into an allogeneic subject. Cells for use in the invention can be derived from a donor of any gestational age, e.g., they can be adult cells, neonatal cells, fetal cells, embryonic stem cells, or muscle cells derived from embryonic stem cells (e.g., as described by Klug et al. 1996. J. Clin. Invest.98:216).

Standard methods can be used to prepare the muscle cells of the invention. Muscle cells can be isolated from donor muscle tissue using standard methods, e.g., enzymatic digestion. For example, in preparing skeletal myoblasts, skeletal muscle cells can be isolated from hind leg muscle or cardiomyocytes can be prepared from of heart tissue. Tissue can be placed into digestion medium (e.g., containing collagenase, trypsin, and protein) and cut into pieces, e.g., with surgical blade. The biopsy pieces can be teased into fine fragments, e.g., using the needle tips of two tuberculin syringe needle assemblies. Cells released from the digestion medium can be collected. This step can be repeated to maximize myoblast purification. Isolated cells can be pooled into groups and expanded as described below.

The invention further provides a-transplantable muscle-cell compositions. Preferably, such compositions comprise muscle cells that have been cultured in vitro for less than about 20 population doublings prior to transplantation. In one embodiment, the muscle cells are permitted to undergo less than about 10 population doublings in vitro prior to transplantation. In another embodiment, the muscle cells are permitted to undergo less than about 5 population doublings in vitro prior to transplantation. In yet another embodiment, the muscle cells of the invention are permitted to undergo between about 1 and about 5 population doublings in vitro prior to transplantation. In another embodiment, the muscle cells of the invention are permitted to undergo between about 2 and about 4 population doublings in vitro prior to transplantation. The optimal number of doublings may vary depending upon the mammal from which the cells were isolated; the optimal numbers of doublings set forth here are for human cells. A rough calculation for cells from other species can be made by comparing the number of doublings before senescence is reached for that species with the number of doublings before senescence is reached in human cells and adjusting the number of doublings accordingly. For example, if cells from a different species go through about half as many doublings as human cells before reaching senescence, then the preferred number of population doublings for that species would be about half of those set forth above.

In one embodiment, such compositions comprise skeletal muscle cells and fibroblast cells and can comprise from about 20% to about 70% myoblasts and, preferably, from about 40–60% myoblasts or about 50% myoblasts. In another embodiment the composition comprises at least about 20%, 25%, 30%, 35%, 40%, 45%, 50%, 55%, 60%, 65%, 70%, 75%, 80%, 85%, 90%, 95%, 96%, 97%, 98% or 99% myoblasts. Compositions having these percentages of myoblasts can be made, e.g., using standard cell sorting techniques to obtain purified populations of cells. The purified populations of cells can then be mixed to obtain compositions comprising the desired percentage of myoblasts. Alternatively, compositions comprising the desired percentage of myoblasts can be obtained by culturing a freshly isolated population of skeletal myoblasts in vitro for a limited number of population doublings such that the percentage of myoblasts in the composition falls within the desired range.

In yet another embodiment, muscle cells can be combined with fibroblasts derived from a tissue source other than muscle tissue, e.g., with fibroblasts from derived from a different tissue source than the muscle cells of the invention, e.g., skin.

The relative percentage of myoblasts and fibroblasts in a composition can be determined, e.g., by staining one or both populations of cells with a cell specific marker and determining the percentage of cells in the composition which express the marker, e.g., using standard techniques such as FACS analysis. For example, an antibody that recognizes a marker present on either myocytes or fibroblasts can be used to detect one or the other or both cell types to thereby determine the relative percentage of each cell type. For example, when an antibody that recognizes myoblasts is used, the percentage of myoblasts in a composition is determined by assessing the percentage of cells which stain with the antibody and the percentage of fibroblasts is determined by subtracting the percentage of myoblasts from 100. In one embodiment, an antibody that recognizes an $\alpha 7\beta 1$ integrin or which recognizes myosin heavy chain present on or in myocytes can be used (Schweitzer et al. 1987. Experimental Cell Research. 172:1). If an internal marker is used, the cells can be permeabilized prior to staining. A primary antibody used for staining can be directly labeled and used for staining or a secondary antibody can be used to detect binding of the primary antibody to cells.

Cells and compositions of the invention can be used fresh, or can be cultured and/or cryopreserved prior to their use in transplantation.

III. Preparation of Cells for Transplantation

The cells of the invention can be expanded in vitro prior to transplantation. In one embodiment, the present invention features a population (i.e., a group of two or more cells) of muscle cells for use in transplantation. The muscle cells of the invention can be grown as a cell culture, i.e, as a population of cells which grow in vitro, in a medium suitable to support the growth of the cells prior to administration to a subject.

Media which can be used to support the growth and/or viability of muscle cells are known in the art and include mammalian cell culture media, such as those produced by Gibco BRL (Gaithersburg, Md.). See 1994 Gibco BRL Catalogue & Reference Guide. The medium can be serum-free but is preferably supplemented with animal serum such as fetal calf serum. Optionally, growth factors can be included. Media which are used to promote proliferation of muscle cells and media which are used for maintenance of cells prior to transplantation can differ. A preferred growth medium for the muscle cells is MCDB 120+ dexamethasone, e.g., 0.39 µg/ml, + Epidermal Growth Factor (EGF), e.g., 10 ng/ml, + fetal calf serum, e.g., 15%. A preferred medium for muscle cell maintenance is DMEM supplemented with protein, e.g., 10% horse serum. Other exemplary media are taught, for example, in Henry et al. 1995. Diabetes. 44:936; WO 98/54301; and Li et al. 1998. *Can. J. Cardiol.* 14:735).

In one embodiment, skeletal myoblast cells can be seeded on laminin coated plates for expansion in myoblast growth Basal Medium containing 10% FBS, dexamethasone and EGF. Myoblast enriched plates are expanded for 48 hours and harvested for transplantation. Cells can be harvested using 0.05% trypsin-EDTA and washed in medium containing FBS. These isolations may contain 30 to 50% myoblasts as verified by myotube fusion formation and flow cytometry using a myoblast or fibroblast specific monoclonal antibody When cardiomyocytes are grown in culture, preferably at least about 20%, more preferably at least about 30%, yet more preferably at least about 40%, still more preferably at least about 50%, and most preferably at least about 60% or more of the cardiomyocytes express cardiac troponin and/or myosin, among other cardiac-specific cell products.

In one embodiment, muscle cells of the invention are cultured on a surface coated with poly L lysine and laminin in a medium comprising EGF. The surface coated can alternatively be coated with collagen with a medium comprising FGF. The surface can be a petri dish or a surface suitable for large scale culture of cells. The culture time in vitro is a maximum of about 14 days and is preferably about 7 days. The cells can be permitted to double population about one time in vitro up to about 10 times in vitro. Preferably, the cells are permitted to double population about 5 times in vitro. Preferably, the cells are permitted to double population up to about 10 times such that the fibroblast to myoblast ratio is approximately 1:2 to 1:1.

IV. Modification of Cells

The invention also provides for altering an antigen on the surface of a cell by modifying, masking, or eliminating an antigen on the surface of a cell in the composition is such that upon transplantation of the composition into a subject lysis of the cell is inhibited. Preferably, the antigen is masked with an antibody or a fragment or derivative thereof that binds to the antigen, more preferably the antibody is a monoclonal antibody, and even more preferably the antibody is an anti-MHC class I antibody or a fragment thereof. Preferably, the fragment is a F(ab')2 fragment. Such masking, modifying or eliminating is preferably done to allogeneic cells or stem cells.

In an unmodified or unaltered state, the antigen on the cell surface stimulates an immune response against the cell (also referred to herein as the donor cell) when the cell is administered to a subject (also referred to herein as the recipient, host, or recipient subject). By altering the antigen, the normal immunological recognition of the donor cell by the immune system cells of the recipient is disrupted and additionally, "abnormal" immunological recognition of this altered form of the antigen can lead to donor cell-specific long term unresponsiveness in the recipient. Thus, alteration of an antigen on the donor cell prior to administering the cell to a recipient interferes with the initial phase of recognition of the donor cell by the cells of the host's immune system subsequent to administration of the cell. Furthermore, alteration of the antigen can induce immunological nonresponsiveness or tolerance, thereby preventing the induction of the effector phases of an immune response (e.g., cytotoxic T cell generation, antibody production etc.) which are ultimately responsible for rejection of foreign cells in a normal immune response. As used herein, the terms "altered" and "modified" are used interchangeably and encompass changes that are made to a donor cell antigen which reduce the immunogenicity of the antigen to thereby interfere with immunological recognition of the antigen by the recipient's immune system. Preferably immunological nonresponsiveness to the donor cells in the recipient subject is generated as a result of alteration of the antigen. The terms "altered" and "modified" are not intended to include complete elimination of the antigen on the donor cell since delivery of an inappropriate or insufficient signal to the host's immune cells may be necessary to achieve immunological nonresponsiveness.

Antigens to be altered according to the invention include antigens on a donor cell which can interact with an immune cell (e.g., a hematopoietic cell, an NK cell, an LAK cell) in an allogeneic or xenogeneic recipient and thereby stimulate a specific immune response against the donor cell in the recipient. The interaction between the antigen and the immune cell may be an indirect interaction (e.g., mediated by soluble factors which induce a response in the hematopoietic cell, e.g., humoral mediated) or, preferably, is a direct interaction between the antigen and a molecule present on the surface of the immune cell (i.e., cell-cell mediated). As used herein, the phrase "immune cell" is intended to include hematopoietic cells such as T lymphocytes, B lymphocytes, monocytes, macrophages, dendritic cells, and other antigen presenting cells, NK cells, and LAK cells. In preferred embodiments, the antigen is one which interacts with a T lymphocyte in the recipient (e.g., the antigen normally binds to a receptor on the surface of a T lymphocyte), or with an NK cell or LAK cell in the recipient.

In a preferred embodiment, the antigen on the donor cell to be altered is an MHC class I antigen. MHC class I antigens are present on almost all cell types. In a normal immune response, self MHC molecules function to present antigenic peptides to a T cell receptor (TCR) on the surface of self T lymphocytes. In immune recognition of allogeneic or xenogeneic cells, foreign MHC antigens (most likely together with a peptide bound thereto) on donor cells are recognized by the T cell receptor on host T cells to elicit an immune response. In addition, foreign MHC class I antigens are known to be recognized by MHC class I receptors on NK cells. MHC class I antigens on a donor cell are altered to interfere with their recognition by T cells, NK cells, or LAK cells in an allogeneic or xenogeneic host (e.g., a portion of the MHC class I antigen which is normally recognized by the T cell receptor, NK cells, or LAK cells is blocked or "masked" such that normal recognition of the MHC class I antigen can no longer occur). Additionally, an altered form of an MHC class I antigen which is exposed to host T cells, NK cells or LAK cells (i.e., available for presentation to the host cell receptor) may deliver an inappropriate or insufficient signal to the host T cell such that, rather than stimulating an immune response against the allogeneic or xenogeneic cell, donor cell-specific T cell non-responsiveness, inhibition of NK-mediated cell rejection, and/or inhibition of LAK-mediated cell rejection is induced. For example, it is known that T cells which receive an inappropriate or insufficient signal through their T cell receptor (e.g., by binding to an MHC antigen in the absence of a costimulatory signal, such as that provided by B7) become anergic rather than activated and can remain refractory to restimulation for long periods of time (see, e.g., Damle et al. (1981) *Proc. Natl. Acad. Sci. USA* 78:5096–5100; Lesslauer et al. (1986) *Eur. J. Immunol.* 16:1289–1295; Gimmi, et al. (1991) *Proc. Natl. Acad. Sci. USA* 88: 6575–6579; Linsley et al. (1991) *J. Exp. Med.* 173:721–730; Koulova et al. (1991) *J. Exp. Med.* 173:759–762; Razi-Wolf, et al. (1992) *Proc. Natl. Acad. Sci. USA* 89:4210–4214).

Alternative to MHC class I antigens, the antigen to be altered on a donor cell can be an MHC class II antigen. Similar to MHC class I antigens, MHC class II antigens function to present antigenic peptides to a T cell receptor on T lymphocytes. However, MHC class II antigens are present on a limited number of cell types (primarily B cells, macrophages, dendritic cells, Langerhans cells and thymic epithelial cells). In addition to or alternative to MHC antigens, other antigens on a donor cell which interact with molecules on host T cells or NK cells and which are known to be involved in immunological rejection of allogeneic or xenogeneic cells can be altered. Other donor cell antigens known to interact with host T cells and contribute to rejection of a donor cell include molecules which function to increase the avidity of the interaction between a donor cell and a host T cell. Due to this property, these molecules are typically referred to as adhesion molecules (although they may serve other functions in addition to increasing the adhesion between a donor cell and a host T cell). Examples of preferred adhesion molecules which can be altered according to the invention include LFA-3 and ICAM-1. These molecules are ligands for the CD2 and LFA-1 receptors, respectively, on T cells. By altering an adhesion molecule on the donor cell, (such as LFA-3, ICAM-1 or a similarly functioning molecule), the ability of the host's T cells to bind to and interact with the donor cell is reduced. Both LFA-3 and ICAM-1 are found on endothelial cells found within blood vessels in transplanted organs such as kidney and heart. Altering these antigens can facilitate transplantation of any vascularized implant, by altering recognition of those antigens by CD2+ and LFA-1+ host T-lymphocytes.

The presence of MHC molecules or adhesion molecules such as LFA-3, ICAM-1 etc. on a particular donor cell can be assessed by standard procedures known in the art. For example, the donor cell can be reacted with a labeled antibody directed against the molecule to be detected (e.g., MHC molecule, ICAM-1, LFA-1 etc.) and the association of the labeled antibody with the cell can be measured by a suitable technique (e.g., immunohistochemistry, flow cytometry etc.).

A preferred method for altering an antigen on a donor cell to inhibit an immune response against the cell is to contact the cell with a molecule which binds to the antigen on the cell surface. It is preferred that the cell be contacted with the molecule which binds to the antigen prior to administering the cell to a recipient (i.e., the cell is contacted with the molecule in vitro). For example, the cell can be incubated with the molecule which binds the antigen under conditions which allow binding of the molecule to the antigen and then any unbound molecule can be removed. Following administration of the modified cell to a recipient, the molecule remains bound to the antigen on the cell for a sufficient time to interfere with immunological recognition by host cells and induce non-responsiveness in the recipient.

Preferably, the molecule for binding to an antigen on a donor cell is an antibody, or fragment or derivative thereof which retains the ability to bind to the antigen. For use in therapeutic applications, it is necessary that the antibody which binds the antigen to be altered be unable to fix complement, thus preventing donor cell lysis. Antibody complement fixation can be prevented by deletion of an Fc portion of an antibody, by using an antibody isotype which is not capable of fixing complement, or by using a complement fixing antibody in conjunction with a drug which inhibits complement fixation. Alternatively, amino acid residues within the Fc region which are necessary for activating complement (see e.g., Tan et al. (1990) *Proc. Natl. Acad. Sci. USA* 87:162–166; Duncan and Winter (1988) *Nature* 332:738–740) can be mutated to reduce or eliminate the complement-activating ability of an intact antibody. Likewise, amino acids residues within the Fc region which are necessary for binding of the Fc region to Fc receptors (see e.g., Canfield, S. M. and S. L. Morrison (1991) *J. Exp. Med.* 173:1483–1491; and Lund, J. et al. (1991) *J. Immunol.* 147:2657–2662) can also be mutated to reduce or eliminate Fc receptor binding if an intact antibody is to be used.

A preferred antibody fragment for altering an antigen is an F(ab')$_2$ fragment. Antibodies can be fragmented using conventional techniques. For example, the Fc portion of an antibody can be removed by treating an intact antibody with pepsin, thereby generating an F(ab')$_2$ fragment. In a standard procedure for generating F(ab')$_2$ fragments, intact antibodies are incubated with immobilized pepsin and the digested antibody mixture is applied to an immobilized protein A column. The free Fc portion binds to the column while the F(ab')$_2$ fragments passes through the column. The F(ab')$_2$ fragments can be further purified by HPLC or FPLC. F(ab')$_2$ fragments can be treated to reduce disulfide bridges to produce Fab' fragments.

An antibody, or fragment or derivative thereof, to be used to alter an antigen can be derived from polyclonal antisera containing antibodies reactive with a number of epitopes on an antigen. Preferably, the antibody is a monoclonal antibody directed against the antigen. Polyclonal and monoclonal antibodies can be prepared by standard techniques known in the art. For example, a mammal, (e.g., a mouse, hamster, or rabbit) can be immunized with the antigen or with a cell which expresses the antigen (e.g., on the cell surface) to elicit an antibody response against the antigen in the mammal. Alternatively, tissue or a whole organ which expresses the antigen can be used to elicit antibodies. The progress of immunization can be monitored by detection of antibody titers in plasma or serum. Standard ELISA or other immunoassay can be used with the antigen to assess the levels of antibodies. Following immunization, antisera can be obtained and, if desired, polyclonal antibodies isolated from the sera. To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art. For example, the hybridoma technique originally developed by Kohler and Milstein ((1975) *Nature* 256:495–497) as well as other techniques such as the human B-cell hybridoma technique (Kozbar et al., (1983) *Immunol. Today* 4:72), and the EBV-hybridoma technique to produce human monoclonal antibodies (Cole et al. (1985) *Monoclonal Antibodies in Cancer Therapy*, Allen R. Bliss, Inc., pages 77–96) can be used. Hybridoma cells can be screened immunochemically for production of antibodies specifically reactive with the antigen and monoclonal antibodies isolated.

Another method of generating specific antibodies, or antibody fragments, reactive against the antigen is to screen expression libraries encoding immunoglobulin genes, or portions thereof, expressed in bacteria with the antigen (or a portion thereof). For example, complete Fab fragments, $V_H$ regions, $F_V$ regions and single chain antibodies can be expressed in bacteria using phage expression libraries. See e.g, Ward et al., (1989) *Nature* 341:544–546; Huse et al., (1989) *Science* 246:1275–1281; and McCafferty et al. (1990) *Nature* 348:552–554. Alternatively, a SCID-hu mouse can be used to produce antibodies, or fragments thereof (available from Genpharn). Antibodies of the appropriate binding specificity which are made by these techniques can be used to alter an antigen on a donor cell.

An antibody, or fragment thereof, produced in a non-human subject can be recognized to varying degrees as foreign when the antibody is administered to a human subject (e.g., when a donor cell with an antibody bound thereto is administered to a human subject) and an immune response against the antibody may be generated in the subject. One approach for minimizing or eliminating this problem is to produce chimeric or humanized antibody derivatives, i.e., antibody molecules comprising portions which are derived from non-human antibodies and portions which are derived from human antibodies. Chimeric antibody molecules can include, for example, an antigen binding domain from an antibody of a mouse, rat, or other species, with human constant regions. A variety of approaches for making chimeric antibodies have been described. See e.g., Morrison et al., *Proc. Natl. Acad. Sci. U.S.A.* 81, 6851 (1985); Takeda et al., *Nature* 314, 452 (1985), Cabilly et al, U.S. Pat. No. 4,816,567; Boss et al, U.S. Pat. No. 4,816,397; Tanaguchi et al., European Patent Publication EP 171496; European Patent Publication 0173494, United Kingdom Patent GB 2177096B. For use in therapeutic applications, it is preferred that an antibody used to alter a donor cell antigen not contain an Fc portion. Thus, a humanized $F(ab')_2$ fragment in which parts of the variable region of the antibody, especially the conserved framework regions of the antigen-binding domain, are of human origin and only the hypervariable regions are of non-human origin is a preferred antibody derivative. Such altered immunoglobulin molecules can be made by any of several techniques known in the art, (e.g., Teng et al., *Proc. Natl. Acad. Sci. U.S.A.*, 80, 7308–7312 (1983); Kozbor et al., *Immunology Today*, 4, 7279 (1983); Olsson et al, *Meth. Enzymol.*, 92, 3–16 (1982)), and are preferably made according to the teachings of PCT Publication W092/06193 or EP 0239400. Humanized antibodies can be commercially produced by, for example, Scotgen Limited, 2 Holly Road, Twickenham, Middlesex, Great Britain.

Each of the cell surface antigens to be altered, e.g., MHC class I antigens, MHC class II antigens, LFA-3 and ICAM-1 are well-characterized molecules and antibodies to these antigens are commercially available. For example, an antibody directed against human MHC class I antigens (i.e., an anti-HLA class I antibody),W6/32, is available from the American Type Culture Collection (ATCC HB 95). This antibody was raised against human tonsillar lymphocyte membranes and binds to HLA-A, HLA-B and HLA-C (Barnstable, C. J. et al. (1978) Cell 14:9–20). Another anti-MHC class I antibody which can be used is PT85 (see Davis, W. C. et al. (1984) *Hybridoma Technology in Agricultural and Veterinary Research*. N. J. Stem and H. R. Gamble, eds., Rownman and Allenheld Publishers, Totowa, N.J., p121; commercially available from Veterinary Medicine Research Development, Pullman, Wash.). This antibody was raised against swine leukocyte antigens (SLA) and binds to class I antigens from several different species (e.g., pig, human, mouse, goat). An anti-ICAM-1 antibody can be obtained from AMAC, Inc., Maine. Hybridoma cells producing anti-LFA-3 can be obtained from the American Type Culture Collection, Rockville, Md. In a preferred embodiment, the antibody is PT85.

A suitable antibody, or fragment or derivative thereof, for use in the invention can be identified based upon its ability to inhibit the immunological rejection of allogeneic or xenogeneic cells. Briefly, the antibody (or antibody fragment) is incubated for a short period of time (e.g., 30 minutes at room temperature) with cells or tissue to be transplanted and any unbound antibody is washed away. The cells or tissue are then transplanted into a recipient animal. The ability of the antibody pretreatment to inhibit or prevent rejection of the transplanted cells or tissue is then determined by monitoring for rejection of the cells or tissue compared to untreated controls.

It is preferred that an antibody, or fragment or derivative thereof, which is used to alter an antigen have an affinity for binding to the antigen of at least 10–7 M. The affinity of an antibody or other molecule for binding to an antigen can be determined by conventional techniques (see Masan, D. W. and Williams, A. F. (1980) *Biochem. J.* 187:1–10). Briefly, the antibody to be tested is labeled with 1251 and incubated with cells expressing the antigen at increasing concentrations until equilibrium is reached. Data are plotted graphically as [bound antibody]/[free antibody] versus [bound antibody] and the slope of the line is equal to the kD (Scatchard analysis).

Other molecules which bind to an antigen on a donor cell and produce a functionally similar result as antibodies, or fragments or derivatives thereof, (e.g., other molecules which interfere with the interaction of the antigen with a hematopoietic cell and induce immunological nonresponsiveness) can be used to alter the antigen on the donor cell. One such molecule is a soluble form of a ligand for an antigen (e.g., a receptor) on the donor cell which could be used to alter the antigen on the donor cell. For example, a soluble form of CD2 (i.e., comprising the extracellular domain of CD2 without the transmembrane or cytoplasmic domain) can be used to alter LFA-3 on the donor cell by binding to LFA-3 on donor cells in a manner analogous to an antibody. Alternatively, a soluble form of LFA-1 can be used to alter ICAM-1 on the donor cell. A soluble form of a ligand can be made by standard recombinant DNA procedures, using a recombinant expression vector containing DNA encoding the ligand encompassing an extracellular domain (i.e., lacking DNA encoding the transmembrane and cytoplasmic domains). The recombinant expression vector encoding the extracellular domain of the ligand can be introduced into host cells to produce a soluble ligand, which can then be isolated. Soluble ligands of use have a binding affinity for the receptor on the donor cell sufficient to remain bound to the receptor to interfere with immunological recognition and induce non-responsiveness when the cell is administered to a recipient (e.g., preferably, the affinity for binding of the soluble ligand to the receptor is at least about $10^{-7}$ M). Additionally, the soluble ligand can be in the form of a fusion protein comprising the receptor binding portion of the ligand fused to another protein or portion of a protein. For example, an immunoglobulin fusion protein which includes an extracellular domain, or functional portion of CD2 or LFA-1 linked to an immunoglobulin heavy chain constant region (e.g., the hinge, CH2 and CH3 regions of a human immunoglobulin such as IgG1) can be used. Immunoglobulin fusion proteins can be prepared, for example, according to the teachings of Capon, D. J. et al. (1989) *Nature* 337:525–531 and U.S. Pat. No. 5,116,964 to Capon and Lasky.

Another type of molecule which can be used to alter an MHC antigen (e.g., and MHC class I antigen) is a peptide which binds to the MHC antigen and interferes with the interaction of the MHC antigen with a T lymphocyte, NK cell, or LAK cell. In one embodiment, the soluble peptide mimics a region of the T cell receptor which contacts the MHC antigen. This peptide can be used to interfere with the interaction of the intact T cell receptor (on a T lymphocyte) with the MHC antigen. Such a peptide binds to a region of the MHC molecule which is specifically recognized by a portion of the T cell receptor (e.g., the alpha-1 or alpha-2 domain of an MHC class I antigen), thereby altering the MHC class I antigen and inhibiting recognition of the antigen by the T cell receptor. In another embodiment, the soluble peptide mimics a region of a T cell surface molecule which contacts the MHC antigen, such as a region of the CD8 molecule which contacts an MHC class I antigen or a region of a CD4 molecule which contacts an MHC class II antigen. For example, a peptide which binds to a region of the alpha-3 loop of an MHC class I antigen can be used to inhibit binding to CD8 to the antigen, thereby inhibiting recognition of the antigen by T cells. T cell receptor-derived peptides have been used to inhibit MHC class I-restricted immune responses (see e.g., Clayberger, C. et al. (1993) *Transplant Proc.* 25:477–478) and prolong allogeneic skin graft survival in vivo when injected subcutaneously into the recipient (see e.g., Goss, J. A. et al. (1993) *Proc. Natl. Acad. Sci. USA* 90:9872–9876).

An antigen on a donor cell further can be altered by using two or more molecules which bind to the same or different antigen. For example, two different antibodies with specificity for two different epitopes on the same antigen can be used (e.g., two different anti-MHC class I antibodies can be used in combination). Alternatively, two different types of molecules which bind to the same antigen can be used (e.g., an anti-MHC class I antibody and an MHC class I-binding peptide). A preferred combination of anti-MHC class I antibodies which can be used with human cells is the W6/32 antibody and the PT85 antibody or F(ab')$_2$ fragments thereof. When the donor cell to be administered to a subject bears more than one hematopoietic cell-interactive antigen, two or more treatments can be used together. For example, two antibodies, each directed against a different antigen (eg., an anti-MHC class I antibody and an anti-ICAM-1 antibody) can be used in combination or two different types of molecules, each binding to a different antigen, can be used (e.g., an anti-ICAM-1 antibody and an MHC class I-binding peptide). Alternatively, polyclonal antisera generated against the entire donor cell or tissue containing donor cells can be used, following removal of the Fc region, to alter multiple cell surface antigens of the donor cells.

The ability of two different monoclonal antibodies which bind to the same antigen to bind to different epitopes on the antigen can be determined using a competition binding assay. Briefly, one monoclonal antibody is labeled and used to stain cells which express the antigen. The ability of the unlabeled second monoclonal antibody to inhibit the binding of the first labeled monoclonal antibody to the antigen on the cells is then assessed. If the second monoclonal antibody binds to a different epitope on the antigen than does the first antibody, the second antibody will be unable to competitively inhibit the binding of the first antibody to the antigen.

A preferred method for altering at least two different epitopes on an antigen on a donor cell to inhibit an immune response against the cell is to contact the cell with at least two different molecules which bind to the epitopes. It is preferred that the cell be contacted with at least two different molecules which bind to the different epitopes prior to administering the cell to a recipient (i.e., the cell is contacted with the molecule in vitro). For example, the cell can be incubated with the molecules which bind to the epitopes under conditions which allow binding of the molecules to the epitopes and then any unbound molecules can be removed. Following administration of the donor cell to a recipient, the molecules remain bound to the epitopes on the surface antigen for a sufficient time to interfere with immunological recognition by host cells and induce non-responsiveness in the recipient.

Alternative to binding a molecule (e.g., an antibody) to an antigen on a donor cell to inhibit immunological rejection of the cell, the antigen on the donor cell can be altered by other means. For example, the antigen can be directly altered (e.g., mutated) such that it can no longer interact normally with an immune cell, e.g., a T lymphocyte), an NK cell, or an LAK cell, in an allogeneic or xenogeneic recipient and induces immunological non-responsiveness to the donor cell in the recipient. For example, a mutated form of a class I MHC antigen or adhesion molecule (e.g., LFA-3 or ICAM-1) which does not contribute to T cell activation but rather delivers an inappropriate or insufficient signal to a T cell upon binding to a receptor on the T cell can be created by mutagenesis and selection. A nucleic acid encoding the mutated form of the antigen can then be inserted into the genome of a non-human animal, either as a transgene or by homologous recombination (to replace the endogenous gene encoding the wild-type antigen). Cells from the non-human animal which express the mutated form of the antigen can then be used as donor cells for transplantation into an allogeneic or xenogeneic recipient.

Alternatively, an antigen on the donor cell can be altered by downmodulating or altering its level of expression on the surface of the donor cell such that the interaction between the antigen and a recipient immune cell is modified. By decreasing the level of surface expression of one or more antigens on the donor cell, the avidity of the interaction between the donor cell and the immune cell e.g., T lymphocyte, NK cell, LAK cell, is reduced. The level of surface expression of an antigen on the donor cell can be down-modulated by inhibiting the transcription, translation or transport of the antigen to the cell surface. Agents which decrease surface expression of the antigen can be contacted with the donor cell. For example, a number of oncogenic viruses have been demonstrated to decrease MHC class I expression in infected cells (see e.g., Travers et al. (1980) Int'l. Symp. on Aging in Cancer, 175180; Rees et al. (1988) Br. J. Cancer, 57:374–377). In addition, it has been found that this effect on MHC class I expression can be achieved using fragments of viral genomes, in addition to intact virus. For example, transfection of cultured kidney cells with fragments of adenovirus causes elimination of surface MHC class I antigenic expression (Whoshi et al (1988) J. Exp. Med 168:2153–2164). For purposes of decreasing MHC class I expression on the surfaces of donor cells, viral fragments which are non-infectious are preferable to whole viruses.

Alternatively, the level of an antigen on the donor cell surface can be altered by capping the antigen. Capping is a term referring to the use of antibodies to cause aggregation and inactivation of surface antigens. To induce capping, a tissue is contacted with a first antibody specific for an antigen to be altered, to allow formation of antigen-antibody immune complexes. Subsequently, the tissue is contacted with a second antibody which forms immune complexes with the first antibody. As a result of treatment with the second antibody, the first antibody is aggregated to form a cap at a single location on the cell surface. The technique of capping is well known and has been described, e.g., in Taylor et al. (1971), Nat. New Biol. 233:225–227; and Santiso et al. (1986), Blood, 67:343–349. To alter MHC class I antigens, donor cells are incubated with a first antibody (e.g., W6/32 antibody, PT85 antibody) reactive with MHC class I molecules, followed by incubation with a second antibody reactive with the donor species, e.g., goat anti-mouse antibody, to result in aggregation.

V. Genetic Modification of Cells

Muscle cells of the invention (or other cells included in the muscle cell compositions of the invention) can be "modified to express a gene product". As used herein, the term "modified to express a gene product" is intended to mean that the cell is treated in a manner that results in the production of a gene product by the cell. Preferably, the cell does not express the gene product prior to modification. Alternatively, modification of the cell may result in an increased production of a gene product already expressed by the cell or result in production of a gene product (e.g., an antisense RNA molecule) which decreases production of another, undesirable gene product normally expressed by the cell.

In one embodiment, skeletal muscle cells are modified to produce a gene product that makes them more cardiac-like, e.g., connexin43 (J. Cell. Biol. 1989. 108:595).

In a preferred embodiment, a cell is modified to express a gene product by introducing genetic material, such as a nucleic acid molecule (e.g., RNA or, more preferably, DNA) into the cell. The nucleic acid molecule introduced into the cell encodes a gene product to be expressed by the cell. The term "gene product" as used herein is intended to include proteins, peptides and functional RNA molecules. Generally, the gene product encoded by the nucleic acid molecule is the desired gene product to be supplied to a subject. Alternatively, the encoded gene product is one which induces the expression of the desired gene product by the cell (e.g., the introduced genetic material encodes a transcription factor which induces the transcription of the gene product to be supplied to the subject).

Examples of gene products that can be delivered to a subject via a genetically modified muscle cells include gene products that can prevent future cardiac disorders, such as growth factors which encourage blood vessels to invade the heart muscle, e.g., Fibroblast Growth Factor (FGF) 1, FGF-2, Transforming Growth Factorβ (TGF-β), and angiotensin. Other gene products that can be delivered to a subject via a genetically modified cardiomyocyte include factors which promote cardiomyocyte survival, such as FGF, TGF-β, IL-10, CTLA 4-Ig, and bcl-2.

A nucleic acid molecule introduced into a cell is in a form suitable for expression in the cell of the gene product encoded by the nucleic acid. Accordingly, the nucleic acid molecule includes coding and regulatory sequences required for transcription of a gene (or portion thereof) and, when the gene product is a protein or peptide, translation of the gene product encoded by the gene. Regulatory sequences which can be included in the nucleic acid molecule include promoters, enhancers and polyadenylation signals, as well as sequences necessary for transport of an encoded protein or peptide, for example N-terminal signal sequences for transport of proteins or peptides to the surface of the cell or for secretion.

Nucleotide sequences which regulate expression of a gene product (e.g., promoter and enhancer sequences) are selected based upon the type of cell in which the gene product is to be expressed and the desired level of expression of the gene product. For example, a promoter known to confer cell-type specific expression of a gene linked to the promoter can be used. A promoter specific for myoblast gene expression can be linked to a gene of interest to confer muscle-specific expression of that gene product. Muscle-specific regulatory elements which are known in the art include upstream regions from the dystrophin gene (Klamut et al., (1989) *Mol. Cell. Biol.* 9:2396), the creatine kinase gene (Buskin and Hauschka, (1989) *Mol. Cell Biol.* 9:2627) and the troponin gene (Mar and Ordahl, (1988) *Proc. Natl. Acad. Sci. USA* 85:6404). Regulatory elements specific for other cell types are known in the art (e.g., the albumin enhancer for liver-specific expression; insulin regulatory elements for pancreatic islet cell-specific expression; various neural cell-specific regulatory elements, including neural dystrophin, neural enolase and A4 amyloid promoters). Alternatively, a regulatory element which can direct constitutive expression of a gene in a variety of different cell types, such as a viral regulatory element, can be used. Examples of viral promoters commonly used to drive gene expression include those derived from polyoma virus, Adenovirus 2, cytomegalovirus and Simian Virus 40, and retroviral LTRs. Alternatively, a regulatory element which provides inducible expression of a gene linked thereto can be used. The use of an inducible regulatory element (e.g., an inducible promoter) allows for modulation of the production of the gene product in the cell. Examples of potentially useful inducible regulatory systems for use in eukaryotic cells include hormone-regulated elements (e.g., see Mader, S. and White, J. H. (1993) *Proc. Natl. Acad. Sci. USA* 90:5603–5607), synthetic ligand-regulated elements (see, e.g. Spencer, D. M. et al. (1993) *Science* 262:1019–1024) and ionizing radiation-regulated elements (e.g., see Manome, Y. et al. (1993) *Biochemistry* 32:10607–10613; Datta, R. et al. (1992) *Proc. Natl. Acad. Sci. USA* 89:10149–10153). Additional tissue-specific or inducible regulatory systems which may be developed can also be used in accordance with the invention.

There are a number of techniques known in the art for introducing genetic material into a cell that can be applied to modify a cell of the invention. In one embodiment, the nucleic acid is in the form of a naked nucleic acid molecule. In this situation, the nucleic acid molecule introduced into a cell to be modified consists only of the nucleic acid encoding the gene product and the necessary regulatory elements. Alternatively, the nucleic acid encoding the gene product (including the necessary regulatory elements) is contained within a plasmid vector. Examples of plasmid expression vectors include CDM8 (Seed, B. (1987) *Nature* 329:840) and pMT2PC (Kaufman, et al (1987) *EMBO J.* 6:187–195). In another embodiment, the nucleic acid molecule to be introduced into a cell is contained within a viral vector. In this situation, the nucleic acid encoding the gene product is inserted into the viral genome (or a partial viral genome). The regulatory elements directing the expression of the gene product can be included with the nucleic acid inserted into the viral genome (i.e., linked to the gene inserted into the viral genome) or can be provided by the viral genome itself.

Naked DNA can be introduced into cells by forming a precipitate containing the DNA and calcium phosphate. Alternatively, naked DNA can also be introduced into cells by forming a mixture of the DNA and DEAE-dextran and incubating the mixture with the cells. or by incubating the cells and the DNA together in an appropriate buffer and subjecting the cells to a high-voltage electric pulse (i.e., by electroporation). A further method for introducing naked DNA cells is by mixing the DNA with a liposome suspension containing cationic lipids. The DNA/liposome complex is then incubated with cells. Naked DNA can also be directly injected into cells by, for example, microinjection. For an in vitro culture of cells, DNA can be introduced by microinjection in vitro or by a gene gun in vivo.

Alternatively, naked DNA can also be introduced into cells by complexing the DNA to a cation, such as polylysine, which is coupled to a ligand for a cell-surface receptor (see for example Wu, G. and Wu, C. H. (1988) *J. Biol. Chem.* 263:1462 1; Wilson et al. (1992) *J. Biol. Chem.* 267:963–967; and U.S. Pat. No. 5,166,320). Binding of the DNA-ligand complex to the receptor facilitates uptake of the DNA by receptor-mediated endocytosis. An alternative method for generating a cell that is modified to express a gene product involving introducing naked DNA into cells is to create a transgenic animal which contains cells modified to express the gene product of interest.

Use of viral vectors containing nucleic acid, e.g., a cDNA encoding a gene product, is a preferred approach for introducing nucleic acid into a cell. Infection of cells with a viral vector has the advantage that a large proportion of cells receive the nucleic acid, which can obviate the need for selection of cells which have received the nucleic acid. Additionally, molecules encoded within the viral vector, e.g., by a cDNA contained in the viral vector, are expressed efficiently in cells which have taken up viral vector nucleic acid and viral vector systems can be used either in vitro or in vivo.

Defective retroviruses are well characterized for use in gene transfer for gene therapy purposes (for a review see Miller, A.D. (1990) *Blood* 76:271). A recombinant retrovirus can be constructed having a nucleic acid encoding a gene product of interest inserted into the retroviral genome. Additionally, portions of the retroviral genome can be removed to render the retrovirus replication defective. The replication defective retrovirus is then packaged into virions which can be used to infect a target cell through the use of a helper virus by standard techniques.

The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) *Proc. Natl. Acad. Sci. USA* 89:6482–6486), hepatocytes (Herz and Gerard (1993) *Proc. Natl. Acad. Sci. USA* 90:2812–2816) and muscle cells (Quantin et al. (1992) *Proc. Natl. Acad. Sci. USA* 89:2581–2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use are deleted for all or parts of the viral E1 and E3 genes but retain as much as 80% of the adenoviral genetic material.

Adeno-associated virus (AAV) is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790).

When the method used to introduce nucleic acid into a population of cells results in modification of a large proportion of the cells and efficient expression of the gene product by the cells (e.g., as is often the case when using a viral expression vector), the modified population of cells may be used without further isolation or subcloning of individual cells within the population. That is, there may be sufficient production of the gene product by the population of cells such that no further cell isolation is needed. Alternatively, it may be desirable to grow a homogenous population of identically modified cells from a single modified cell to isolate cells which efficiently express the gene product. Such a population of uniform cells can be prepared by isolating a single modified cell by limiting dilution cloning followed by expanding the single cell in culture into a clonal population of cells by standard techniques.

Alternative to introducing a nucleic acid molecule into a cell to modify the cell to express a gene product, a cell can be modified by inducing or increasing the level of expression of the gene product by a cell. For example, a cell may be capable of expressing a particular gene product but fails to do so without additional treatment of the cell. Similarly, the cell may express insufficient amounts of the gene product for the desired purpose. Thus, an agent which stimulates expression of a gene product can be used to induce or increase expression of a gene product by the cell. For example, cells can be contacted with an agent in vitro in a culture medium. The agent which stimulates expression of a gene product may function, for instance, by increasing transcription of the gene encoding the product, by increasing the rate of translation or stability (e.g., a post transcriptional modification such as a poly A tail) of an mRNA encoding the product or by increasing stability, transport or localization of the gene product. Examples of agents which can be used to induce expression of a gene product include cytokines and growth factors.

Another type of agent which can be used to induce or increase expression of a gene product by a cell is a transcription factor which upregulates transcription of the gene encoding the product. A transcription factor which upregulates the expression of a gene encoding a gene product of interest can be provided to a cell, for example, by introducing into the cell a nucleic acid molecule encoding the transcription factor. Thus, this approach represents an alternative type of nucleic acid molecule which can be introduced into the cell (for example by one of the previously discussed methods). In this case, the introduced nucleic acid does not directly encode the gene product of interest but rather causes production of the gene product by the cell indirectly by inducing expression of the gene product. In one embodiment, the invention provides a method for promoting a cardiac cell phenotype in a skeletal myoblast by recombinantly expressing a cardiac cell gene product in the myoblast so that the cardiac cell phenotype is promoted. In an embodiment, the gene product is a GATA transcription factor and, preferably is GATA4 or GATA6. The nucleotide sequence encoding GATA6 can be found, e.g., in any public or private database. The sequence is available, e.g., on GenBank as accession number 005257. The sequence is also taught, e.g., in Genomics. 1996. 38(3):283–90. The nucleotide sequence encoding GATA-4 is also available through a variety of databases, e.g., at GenBank accession number L34357.

In another embodiment, the cells can be engineered to recombinantly express an angiogenic gene product, such as, CTGF (*J. Biochem* 1999 July 1;126:137), VEGF (Jpn J Cancer Res 1999 January; 90:93–100), IGR-I, IGF-II, TGF-$\beta$1, PDGF $\beta$, or an agent that acts indirectly to induce an angiogenic agent, e.g., FGF 4 (Cancer Res 1997 December 15;57(24):5590–7).

VI. Cellular Transplantation

The term "subject" is intended to include mammals, particularly humans. Examples of subjects include primates (e.g., humans, and monkeys). Subjects suitable for transplantation using the instant methods having disorders characterized by insufficient cardiac function or cardiac damage or myocardial ischemic damage.

Transplantation of muscle cells of the invention into the heart of a human subject with a cardiac disorder or myocardial ischemia results in replacement of lost cardiomyocytes.

Muscle cells are introduced into a subject with a cardiac disorder in an amount sufficient to result in at least partial reduction or alleviation of at least one adverse effect or symptom of the cardiac disorder. Preferably, the cells are transplanted into an ischemic zone of the heart.

In another embodiment, the muscle cells are introduced into a subject in an amount sufficient to replace lost or damaged cardiomyocytes.

As used herein the terms "administering", "introducing", and "transplanting" are used interchangeably and refer to the placement of the muscle cells of the invention into a subject, e.g., a syngeneic, allogeneic,.or a xenogeneic subject, by a method or route which results in localization of the muscle cells at a desired site, e.g., at the site of cardiac damage in the subject.

In one embodiment the cells of the invention are introduced into a subject having cardiac damage in the left ventricle. In another embodiment, the cells of the invention are introduced into a subject having cardiac damage in the anterior portion of the left ventricle. In another embodiment, the cells of the invention are introduced into a subject having cardiomyopathy, e.g., hypertrophic or dialated in nature. In another embodiment, the cells of the invention are introduced into a subject having myocardial ischemic damage. In yet another embodiment, the cells are administered to a subject having cardiac damage characterized by an ejection fraction of less than 50%, e.g., 40–50%.

VIII Methods of Treatment

The invention further provides a method for treating a condition in a subject characterized by damage to cardiac tissue comprising transplanting a muscle cell or muscle cell composition of the invention into the subject such that the condition is thereby treated. Preferably, the composition is transplanted by direct injection into the damaged cardiac tissue (e.g., cardiac tissue damaged by ischemia, or into fibrotic tissue or scar tissue). In one embodiment, a catheter is used to inject the composition. The damage to the cardiac tissue can be an infarction, myocardial ischemic damage or cardiomyopathy. The cardiac damage to be treated can be located in a ventricle wall. In a preferred method, the cardiac damage is located in a ventricle wall such as the left ventricle wall. In a preferred embodiment autologous cells are transplanted. In another embodiment, the composition is transplanted into a coronary vessel of the subject.

One method that can be used to deliver the muscle cells of the invention to a subject is direct injection of the muscle cells into the ventricular myocardium of the subject. See e.g., Soonpaa, M. H. et al. (1994) *Science* 264:98–101; Koh, G. Y. et al. (1993) *Am. J. Physiol.* 33:H1727–1733. Muscle cells can be administered in a physiologically compatible carrier, such as a buffered saline solution. To treat disorders characterized by insufficient cardiac function in a human subject, about $10^6$–$10^7$ muscle cells can be introduced into the human, e.g., into the human heart.

To accomplish these methods of administration, the muscle cells of the invention can be inserted into a delivery device which facilitates introduction by, injection or implantation, of the cardiomyocytes into the subject. Such delivery devices include tubes, e.g., catheters, for injecting cells and fluids into the body of a recipient subject. In a preferred embodiment, the tubes additionally have a needle, e.g., a syringe, through which the cells of the invention can be introduced into the subject at a desired location. The muscle cells of the invention can be inserted into such a delivery device, e.g., a syringe, in different forms. The needle gauge used in transplantation of the cells can be, e.g., 25 to 30. For example, the cells can be suspended in a solution or embedded in a support matrix when contained in such a delivery device. As used herein, the term "solution" includes a pharmaceutically acceptable carrier or diluent in which the cells of the invention are suspended such that they remain viable. Pharmaceutically acceptable carriers and diluents include saline, aqueous buffer solutions, solvents and/or dispersion media. The use of such carriers and diluents is well known in the art. The solution is preferably sterile and fluid to the extent that easy syringability exists. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the invention can be prepared by incorporating muscle cells as described herein in a pharmaceutically acceptable carrier or diluent and, as required, other ingredients enumerated above, followed by filtered sterilization.

In one embodiment, delivery of the cells directly to the damaged area of the heart can be accomplished with a catheter that can reach the ischemic area of the heart and enter the myocardial tissue. For example, a catheter can be introduced percutaneously and routed through the vascular system or by catheters that reach the heart through surgical incisions such as a limited thoracotomy involving an incision between the ribs.

In a preferred embodiment, a type of catheter that is normally not used to deliver cells is used to deliver the muscle cells of the invention (e.g., catheters which are not known in the art to be appropriate for delivery of cells, but which are used to deliver drugs, biologicals, proteins, or genes). Surprisingly, these catheters provide an excellent mechanism by which cells can be delivered to damaged cardiac tissue, even though the damaged cardiac wall can be quite thin. For example, one type of catheter can be introduced into the femoral artery and threaded into the left ventricle where it is used to deliver cells into the heart from the endocardial surface via a needle that is extruded from the end of the catheter. This type of catheter can be localized to the desired area by fluoroscopy (MicroHeart) or by a sensor (Boston Scientific) that aids in targeting cells to the ischemic zone of the myocardium (BioSense). A second type of catheter is introduced via the cardiac venous system and the cells are injected into the myocardium from the epicardial side through a needle that is extruded from a housing at the end of the catheter upon reaching the ischemic zone. A multineedle catheter may be introduced via a minithoracotomy and the desired depth, pattern and volume can be set to deliver the cells. These catheters can also be used in conjunction with a laser that is used to create openings in the endocardium that allow better access of the cells and stimulate the growth of new blood vessels in the channels formed by the laser.

Support matrices in which the muscle cells can be incorporated or embedded include matrices which are recipient-compatible and which degrade into products which are not harmful to the recipient. Natural and/or synthetic biodegradable matrices are examples of such matrices. Natural biodegradable matrices include, for example, collagen matrices. Synthetic biodegradable matrices include synthetic polymers such as polyanhydrides, polyorthoesters, and polylactic acid. These matrices provide support and protection for the cardiomyocytes in vivo.

The muscle cells can be administered to a subject by any appropriate route which results in delivery of the cells to a desired location in the subject where they engraft. It is preferred that at least about 5%, preferably at least about 10%, more preferably at least about 20%, yet more preferably at least about 30%, still more preferably at least about 40%, and most preferably at least about 50% or more of the cells remain viable after administration into a subject. The period of viability of the cells after administration to a subject can be as short as a few hours, e.g., twenty-four hours, to a few days, to as long as a few weeks to months.

Once delivered, the ability of the cells and compositions of the invention to enhance cardiac function in a subject can be measured by a variety of means known in the art. For example, the ability of the cells to improve systolic myocardial performance or contractility can be measured. In addition, the cells and compositions of the invention can be tested for their ability to improve the diastolic pressure-strain relationship in the subject.

The muscle cells of the invention can further be included in compositions which comprise agents in addition to the muscle cells or muscle cell compositions of the invention. For example, such compositions can include pharmaceutical carriers, antibodies, immunosuppressive agents, or angiogenic factors.

VII Modulation of Immune Response

Prior to introduction into a subject, the muscle cells can be modified to inhibit immunological rejection. The muscle cells can, as described in detail herein, be rendered suitable for introduction into a subject by alteration of at least one immunogenic cell surface antigen (e.g., an MHC class I antigen). To inhibit rejection of transplanted muscle cells and to achieve immunological non-responsiveness in an allogeneic or xenogeneic transplant recipient, the method of the invention can include alteration of immunogenic antigens on the surface of the muscle cells prior to introduction into the subject. This step of altering one or more immunogenic antigens on muscle cells can be performed alone or in combination with administering to the subject an agent which inhibits T cell activity in the subject. Alternatively, inhibition of rejection of a muscle cell graft can be accomplished by administering to the subject an agent which inhibits T cell activity in the subject in the absence of prior alteration of an immunogenic antigen on the surface of the muscle cells. As used herein, an agent which inhibits T cell activity is defined as an agent which results in removal (e.g., sequestration) or destruction of T cells within a subject or inhibits T cell functions within the subject (i.e., T cells may still be present in the subject but are in a non-functional state, such that they are unable to proliferate or elicit or perform effector functions, e.g cytokine production, cytotoxicity etc.). The term "T cell" encompasses mature peripheral blood T lymphocytes. The agent which inhibits T cell activity may also inhibit the activity or maturation of immature T cells (e.g., thymocytes).

A preferred agent for use in inhibiting T cell activity in a recipient subject is an immunosuppressive drug. The term "immunosuppressive drug or agent" is intended to include pharmaceutical agents which inhibit or interfere with normal immune function. A preferred immunsuppressive drug is cyclosporin A. Other immunosuppressive drugs which can be used include FK506, and RS-61443. In one embodiment, the immunosuppressive drug is administered in conjunction with at least one other therapeutic agent. Additional therapeutic agents which can be administered include steroids (e.g., glucocorticoids such as prednisone, methyl prednisolone and dexamethasone) and chemotherapeutic agents (e.g., azathioprine and cyclosphosphamide). In another embodiment, an immunosuppressive drug is administered in conjunction with both a steroid and a chemotherapeutic agent. Suitable immunosuppressive drugs are commercially available (e.g., cyclosporin A is available from Sandoz, Corp., East Hanover, N.J.).

An immunsuppressive drug is administered in a formulation which is compatible with the route of administration. Suitable routes of administration include intravenous injection (either as a single infusion, multiple infusions or as an intravenous drip over time), intraperitoneal injection, intramuscular injection and oral administration. For intravenous injection, the drug can be dissolved in a physiologically acceptable carrier or diluent (e.g., a buffered saline solution) which is sterile and allows for syringability. Dispersions of drugs can also be prepared in glycerol, liquid polyethylene glycols, and mixtures thereof and in oils. Convenient routes of administration and carriers for immunsuppressive drugs are known in the art. For example, cyclosporin A can be administered intravenously in a saline solution, or orally, intraperitoneally or intramuscularly in olive oil or other suitable carrier or diluent.

An immunosuppressive drug is administered to a recipient subject at a dosage sufficient to achieve the desired therapeutic effect (e.g., inhibition of rejection of transplanted cells). Dosage ranges for immunosuppressive drugs, and other agents which can be coadministered therewith (e.g., steroids and chemotherapeutic agents), are known in the art (See e.g., Kahan, B. D. (1989) *New Eng. J. Med.* 321(25): 1725–1738). A preferred dosage range for immunosuppressive drugs, suitable for treatment of humans, is about 1–30 mg/kg of body weight per day. A preferred dosage range for cyclosporin A is about 1–10 mg/kg of body weight per day, more preferably about 1–5 mg/kg of body weight per day. Dosages can be adjusted to maintain an optimal level of the immunosuppressive drug in the serum of the recipient subject. For example, dosages can be adjusted to maintain a preferred serum level for cyclosporin A in a human subject of about 100–200 ng/ml. It is to be noted that dosage values may vary according to factors such as the disease state, age, sex, and weight of the individual. Dosage regimens may be adjusted over time to provide the optimum therapeutic response according to the individual need and the professional judgment of the person administering or supervising the administration of the compositions, and that the dosage ranges set forth herein are exemplary only and are not intended to limit the scope or practice of the claimed composition.

In one embodiment of the invention, an immunsuppressive drug is administered to a subject transiently for a sufficient time to induce tolerance to the transplanted cells in the subject. Transient administration of an immunosuppressive drug has been found to induce long-term graft-specific tolerance in a graft recipient (See Brunson et al. (1991) *Transplantation* 52:545; Hutchinson et al. (1981) *Transplantation* 32:210; Green et al. (1979) *Lancet* 2:123; Hall et al. (1985) *J. Exp. Med.* 162:1683). Administration of the drug to the subject can begin prior to transplantation of the cells into the subject. For example, initiation of drug administration can be a few days (e.g., one to three days) before transplantation. Alternatively, drug administration can begin the day of transplantation or a few days (generally not more than three days) after transplantation. Administration of the drug is continued for sufficient time to induce donor cell-specific tolerance in the recipient such that donor cells will continue to be accepted by the recipient when drug administration ceases. For example, the drug can be administered for as short as three days or as long as three months following transplantation. Typically, the drug is administered for at least one week but not more than one month following transplantation. Induction of tolerance to the transplanted cells in a subject is indicated by the continued acceptance of the transplanted cells after administration of the immunosuppressive drug has ceased. Acceptance of transplanted tissue can be determined morphologically (e.g., with skin grafts by examining the transplanted tissue or by biopsy) or by assessment of the functional activity of the graft.

Another type of agent which can be used to inhibit T cell activity in a subject is an antibody, or fragment or derivative thereof, which depletes or sequesters T cells in a recipient. Antibodies which are capable of depleting or sequestering T cells in vivo when A administered to a subject are known in the art. Typically, these antibodies bind to an antigen on the surface of a T cell. Polyclonal antisera can be used, for example anti-lymphocyte serum. Alternatively, one or more monoclonal antibodies can be used. Preferred T cell-depleting antibodies include monoclonal antibodies which bind to CD2, CD3, CD4 or CD8 on the surface of T cells. Antibodies which bind to these antigens are known in the art and are commercially available (e.g., from American Type Culture Collection). A preferred monoclonal antibody for binding to CD3 on human T cells is OKT3 (ATCC CRL 8001). The binding of an antibody to surface antigens on a T cell can facilitate sequestration of T cells in a subject and/or destruction of T cells in a subject by endogenous mechanisms. Alternatively, a T cell-depleting antibody which binds to an antigen on a T cell surface can be conjugated to a toxin (e.g., ricin) or other cytotoxic molecule (e.g., a radioactive isotope) to facilitate destruction of T cells upon binding of the antibody to the T cells. See U.S. patent application Ser. No. 08/220,724, filed Mar. 31, 1994, for further details concerning the generation of antibodies which can be used in the present invention.

Another type of antibody which can be used to inhibit T cell activity in a recipient subject is an antibody which inhibits T cell proliferation. For example, an antibody directed against a T cell growth factor, such as IL-2, or a T cell growth factor receptor, such as the IL-2 receptor, can inhibit proliferation of T cells (See e.g., DeSilva, D.R. et al. (1991) *J. Immunol.* 147:3261–3267). Accordingly, an IL-2 or an IL-2 receptor antibody can be administered to a recipient to inhibit rejection of a transplanted cell (see e.g. Wood et al. (1992) *Neuroscience* 49:410). Additionally, both an IL-2 and an IL-2 receptor antibody can be coadministered to inhibit T cell activity or can be administered with another antibody (e.g., which binds to a surface antigen on T cells).

An antibody which depletes, sequesters or inhibits T cells within a recipient can be administered at a dose and for an appropriate time to inhibit rejection of cells upon transplantation. Antibodies are preferably administered intravenously in a pharmaceutically acceptable carrier or diluent (e.g., a sterile saline solution). Antibody administration can begin prior to transplantation (e.g., one to five days prior to transplantation) and can continue on a daily basis after transplantation to achieve the desired effect (e.g., up to fourteen days after transplantation). A preferred dosage range for administration of an antibody to a human subject is about 0.1–0.3 mg/kg of body weight per day. Alternatively, a single high dose of antibody (e.g., a bolus at a dosage of about 10 mg/kg of body weight) can be administered to a human subject on the day of transplantation. The effectiveness of antibody treatment in depleting T cells from the peripheral blood can be determined by comparing T cell counts in blood samples taken from the subject before and after antibody treatment. Dosage regimes may be adjusted over time to provide the optimum therapeutic response according to the individual need and the professional judgment of the person administering or supervising the administration of the compositions. Dosage ranges set forth herein are exemplary only and are not intended to limit the scope or practice of the claimed composition.

The present invention is further illustrated by the following examples which in no way should be construed as being further limiting. The contents of all cited references (including literature references, issued patents, published patent applications, and co-pending patent applications) cited throughout this application are hereby expressly incorporated by reference.

Example 1

Cellular Therapy for Myocardial Repair: Successful Transplantation of Myoblasts by Intracoronary Injection into the Heart after Acute Myocardial Infarction Cellular transplantation (CT), a potential strategy for myocardial repair, has not been performed in a large animal model of acute myocardial infarction (AMI). The feasibility of CT with human myoblasis (HM) delivered by intracoronary (IC) injection into infarcted canine myocardium in vivo was investigated.

In in vitro studies: cloned HM isolated from skeletal muscle biopsies were cocultured with fetal cardiomyocytes (FC); 2) in vivo studies: Adult mongrel dogs were subject (via left thoracotomy) to left anterior descending coronary artery (LAD) occlusion for 90 min. followed by sustained reperfusion. At 1 hr or 1 day post AMI, CM ($40 \times 10^6$ cells) transfected with the reporter gene LacZ were bolused by injection into the LAD. Cyclosporine and prednisone were given daily. At 1 hr or 7 days post transplant, hearts were harvested and serial sections examined for β-gal histochemistry.

In coculture HM showed integration and synchronous contractility with FC. 2) in dogs LacZ positive cells showed a) perivasular infiltration of HM; b) extensive engraftment of HM bordering the AMI zone from epicardium to endocardium; and c) permeation of HM into the AMI zone where new vasculture is developing. Thus, in dogs HM can be implanted and survive in the periphery of infarcted myocardium; 2) CT to augment damages myocardial cells can be performed by IC injection.

Example 2

Induction Of Cardiomyocyte Phenotype In Skeletal Myoblasts Using Cardiomyocyte-Specific GATA4/6 Transcription Factors In order to address issues concerning the time and mode of myoblast infusionjstudies were conducted using dog myoblasts under a Cyclosporin A (CyA) and prednisone immunosuppression regimen starting one day before cell transplantation. Dog myoblasts were isolated from male skeletal muscle (TA) biopsies and transplanted into female dogs. Cells for the short-term studies were labeled with CM-DII before transplantation and were detected by fluorescence microscopy. These allogeneic dog myoblast studies (short-term) were proposed to address the time and mode of cell transplantation. The green fluorescent protein (GFP) recombinant adenoviral vector system can be used to provide a powerful detection method for the implanted myoblasts. This approach is highly efficient in infecting the majority (>90%) of the myoblasts with the GFP reporter gene during short incubation at 37° C.

Construction of E1-deleted recombinant adenoviral vector carrying GFP cDNA is known in the art. Similar constructs containing both the E1- and the E3-deleted recombinant vector containing GFP and GATA cDNA, respectively were made. Once the adenoviral vector infects the myoblasts it is replication defective and unable to re infect additional cells. The GFP cDNA was subcloned between NotI and XhoI sites of the bacterial plasmid vector pAd.RSV4, which uses the RSV long-terminal repeat as a promoter and the SV40 polyadenylation signal and contains Ad sequences 0 to 1 and 9 to 16 map units. The plasmid vector was then cotransfected into 293 cells with pJM 17. Recombinant adenoviral vector was then prepared as a high-titer stock by propagation in 293 cells. Viral titer was determined to be 101 pfu/mL by plaque assay.

Additional adenoviral vectors containing the GFP reporter gene as well as the human cardiomyocyte specific transcription factor GATA4 or GATA6 cDNA can be used to infect myoblasts to help differentiate toward a contractile cardiomyocyte phenotype. This includes the endogenous up regulation of the genes encoding the contractile apparatus and the Ca++ ATPase associated with cardiac slow twitch (SERCA).

Example 3

Antigen Masking: Comparison of PT-85 and W6/32 Binding to Human and Porcine Cells The affinities of PT-85 and W6/32 for human and porcine cells were measured by FACS analysis in a single experiment to limit variations from looking at multiple previous experiments. The affinities of PT-85 for porcine versus human cells were compared. Also compared were PT-85 to W6/32 for reactivity with human cells.

The half-maximal binding of PT-85 to endothelial cells was at 0.007 ug of antibody ($10^5$ cells) and to HeLa cells was at 0.005 ug of antibody. The conclusion is that the affinity for cell surface MHC class I is roughly similar for the porcine and human cell.

The relative affinities for the soluble Class I molecules (HO) from porcine vs human cells is not the same. PT-85 precipitates the porcine molecule (from PBLs) with a considerably higher apparent affinity than the human molecule (from JY cells). The lack of correlation between the results for the cell surface and soluble MHC molecules is similar to what was seen in the comparisons of PT-85 and 9-3.

The half maximal binding of W6/32 to HeLa cells was at 0.04 ug of antibody as compared to 0.005 ug for PT-85 ($10^5$ cells). The affinity of PT-85 is therefore slightly higher than W6/32 for human cells. Both antibodies reached saturation at concentrations approaching 1 ug, but W6/32 showed slightly higher fluorescence intensity.

Using immunoprecipitation on JY cells, the binding of W6/32 to soluble HLA is far stronger than PT-85: a dark band is obtained with W6/32 (2 ug antibody) whereas the band for the same concentration of PT-85 is barely detectable.

The results indicate PT-85 and W6/32 display similar affinities for cell surface HLA, and that antibody binding to soluble MHC molecules is useful for identification of the antigens but not for the determination of relative affinities.

The results are consistent with the two color FACS analysis that showed binding of both W6/32 and PT-85 to the same cells, indicating that both epitopes can be masked simultaneously.

Example 4

Transplantation and Survival of Muscle Cells In Recipient Hearts

The following transplantations of cells all into male Lewis rats were performed.

(A) Cells isolated from syngeneic skeletal muscles and grown on laminin with EGF for only 3 days (without dexamethasone) were transplanted and observed as follows:

7A1: 1 wk frozen heart (12.5 mg/kg CyA+4 mg/kg prednisone) and

7A2: 1 wk frozen heart (no immunosuppression).

(B) Cells isolated from syngeneic skeletal muscles and grown on collagen with FGF for only 3 days were transplanted and observed as follows:

7B1: 1 wk frozen heart (12.5 mg/kg CyA+4 mg/kg prednisone);

7B2: 1 wk frozen heart (no immunosuppression);

7B3: 1 wk formalin fixed heart(12.5 mg/kg CyA+4 mg/kg prednisone); and

7B4: 1 wk formalin fixed heart (no immunosuppression).

Cells for use in this experiment were permitted to undergo less than 20 population doublings in vitro and were not sorted prior to transplantation. Immunosuppression in the animal started day −1. Animals were transplanted at day 0 by injection of $2\times10^5$ cells/site (2 needle track/site). Animals were harvested on day 7. Transplantations were sectioned and analyzed by H&E (+trichrome) and immunostained with anti-myogenin (+anti-CD11). All rat heart sections looked very good for cell survival and anti-myogenin staining. No detectable difference between the groups with or without immunosuppression was observed.

Larger areas of survival with 10-fold less transplanted cells relative to experiments using purified cells into syngeneic female rat hearts were noted. The results appear in Table 3.

TABLE 3

Rat Myoblast/Myotube Transplantation Results

| Rat | Cell Injection | Survival Time | Fixation Procedure | H & E Staining | Trichrome Staining | Tagged Beads | Myogenin Staining | MY-32 Staining | MF-20 Staining | CD11 Staining |
|---|---|---|---|---|---|---|---|---|---|---|
| 7A1 | $1.4 \times 10^5$ Myoblasts | 1 week | Freeze | + | N/A/ | − | + (Good cell survival) | N/A | N/A | − (No immune cells) |
| 7A2 | $1.4 \times 10^5$ Myoblasts | 1 week | Freeze | + | N/A/ | − | + (Good cell survival) | N/A | N/A | − (No immune cells) |
| 7B1 | $1.4 \times 10^5$ Myoblasts | 1 week | Freeze | + | N/A/ | − | + (Good cell survival) | N/A | N/A | − (No immune cells) |
| 7B2 | $1.4 \times 10^5$ Myoblasts | 1 week | Freeze | + | N/A/ | − | + (Good cell survival) | N/A | N/A | − (No immune cells) |
| 7B3 | $1.4 \times 10^5$ Myoblasts | 1 week | Formalin | + | Some blue and pink | − | + (Good cell survival) | N/A | N/A | N/A |
| 7B4 | $1.4 \times 10^5$ Myoblasts | 1 week | Formalin | + | Some blue and pink | − | + (Good cell survival) | N/A | N/A | N/A |

Example 5

Comparison of Transplantation Results With and Without Sorting of Cells Prior to Transplantation The following transplantations of cells all into male Lewis rats were performed. In this example, subjects were given experimentally induced myocardial infarctions on day 1. Animals were allowed to recover for one week. Transplantation was performed after the one week resting period.

(A) Cells isolated from syngeneic skeletal muscles and grown on laminin with EGF for only 3 days. $2 \times 10^5$ cells/heart were injected ($10^5$/site) and observed as follows:

8A1: 1 wk survival (Freeze)

8A2: 4 wk survival (Freeze)

8A3: 4 wk survival (Formalin)

8A4: 4 wk survival with immunosuppression (48 hr; Freeze)

8A5: 4 wk survival with immunosuppression (Freeze)

(B) Cells isolated from syngeneic skeletal muscles and grown on laminin with EGF, sorted and expanded. $2 \times 10^5$ cells/heart were injected ($10^5$/site) and observed as follows:

8B1: 1 wk survival (Freeze)

8B2: 4 wk survival (Freeze)

8B3: 4 wk survival (Formalin)

8B4: 4 wk survival with immunosuppression (Freeze)

(C) Cells isolated from syngeneic skeletal muscles and grown on laminin with EGF, sorted and expanded. $2 \times 10^6$ cells/heart were injected ($10^6$/site; 5–10 fold) and observed as follows:

8C1: 1 wk survival (Freeze)

8C2: 4 wk survival (Freeze)

8C3: 4 wk survival (Formalin)

8C4: 4 wk survival with immunosuppression (Freeze)

Immunosuppression (12.5 mg/kg CyA+4 mg/kg prednisone) for positive control. Cells were cultured for 3 days (i.e., were unsorted and cultured for a limited time in vitro so that they undergo a limited number of population doublings) or sorted and expanded for 6–10 days (sorted). Crude cells were injected $10^5$ cells/site (2 needle track/heart) (12.5 μl /site). Sorted Cells: A comparison was made between $10^5$ cells/site versus $10^6$ cells/site (40 μl /site),i.e. 12.5 μl/site vs. 40 μl/site. A1, B1, and C1 hearts were harvested between 1 and 2 weeks. Remaining hearts were harvested by 4 weeks. Hearts were sectioned and analyzed by H&E (+trichrome). Cells were immunostained with anti-myogenin (+anti-CD11). Results are shown in Table 4.

TABLE 4

Rat Myoblast/Myotube Results

| Rat | Cell Injection | Survival Time | Fixation Procedure | H&E Staining | Myogenin Staining |
|---|---|---|---|---|---|
| 8A1 | $2 \times 10^5$ Myoblasts | 1 week | Freeze | + (graft) | + Myoblasts |
| 8A2 | $2 \times 10^5$ Myoblasts | 4 weeks | Freeze | Small graft | |
| 8A3 | $2 \times 10^5$ Myoblasts | 4 weeks | Formalin | + (graft) | |
| 8A4 | $2 \times 10^5$ Myoblasts | 4 weeks | Freeze | + (graft) | |
| 8A5 | $2 \times 10^5$ Myoblasts | 2 days | Freeze | + (graft) | + Myoblasts |
| 8B1 | $2 \times 10^5$ Myoblasts | 1 week | Freeze | + (graft) | + Myoblasts |
| 8B2 | $2 \times 10^5$ Myoblasts | 4 weeks | | | |
| 8B3 | $2 \times 10^5$ Myoblasts | 4 weeks | | | |
| 8B4 | $2 \times 10^5$ Myoblasts | 4 weeks | | | |
| 8C1 | $2 \times 10^6$ Myoblasts | 1 week | Freeze | + (graft) | + Myoblasts |
| 8C2 | $2 \times 10^6$ Myoblasts | 4 weeks | | | |
| 8C3 | $2 \times 10^6$ Myoblasts | 4 weeks | | | |
| 8C4 | $2 \times 10^6$ Myoblasts | 4 weeks | | | |

Figure 1B:
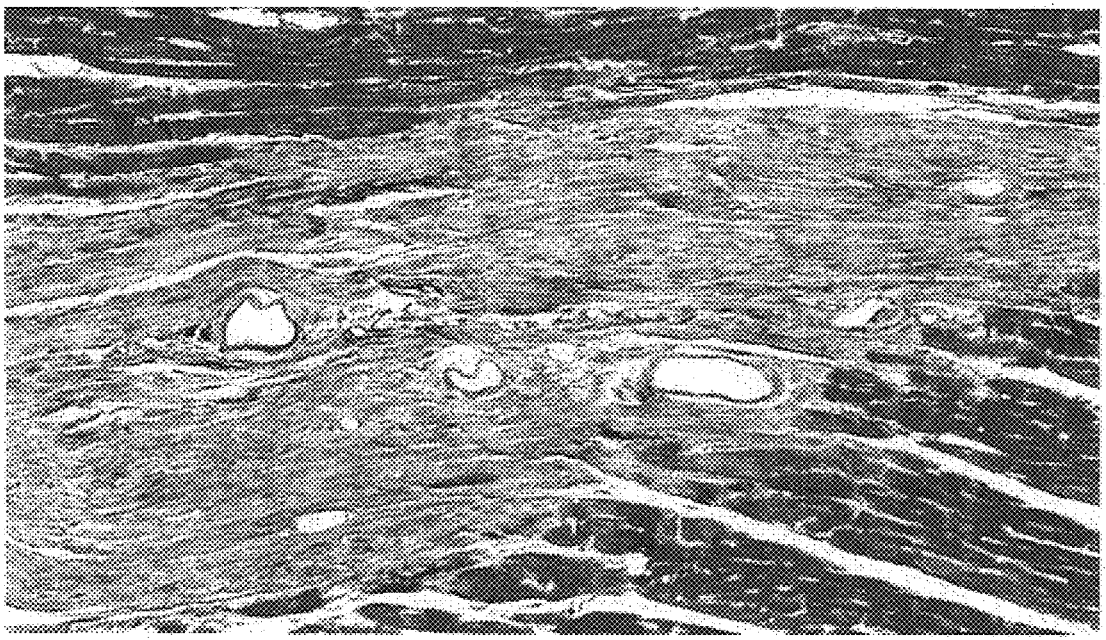

Histology of transplanted grafts indicates that compositions comprising skeletal myoblasts which are permitted to undergo fewer population doublings survive better than such compositions which are sorted to obtain purified cells and permitted to undergo more population doublings. FIG. 1 shows staining of grafts with trichrome. FIG. 1A is a photograph of transplanted cells which were sorted prior to transplantation, while FIG. 1B is a photograph of transplanted cells which were not sorted and were only allowed to undergo several population doublings in vitro prior to transplantation. More grafted cells survive in FIG. 1B.

Figure 2A:
FIGS. 2A–2B shows that vessel formation (angiogenesis) occurs after transplantation of muscle cells.
Figure 2B:

Histological results also indicate that upon the transplantation of compositions comprising skeletal myoblasts into infarcted rat hearts vessel formation (angiogenesis) occurs. FIGS. 2A (lower power) and 2B (higher power) shows staining of such a graft for factor VIII at three weeks post transplantation. Vessels can be seen in the center of the graft.

Exercise max tests were performed on animals which were transplanted with skeletal myoblasts into an infarcted zone in the rat heart. The results of an exemplary test are shown in Table 5. Table 5 compares exercise results for transplanted (myoblast) and control (sham) animals and shows that transplanted animals were able to exercise longer on a treadmill (duration) and go further (distance) than control animals which received a mock transplant.

TABLE 5

Exercise Max Test

| | DURATION (Sec) (mean ± SD) | DISTANCE (Meters) (mean ± SD) |
|---|---|---|
| GROUP 1 (MYOBLAST) | | |
| Baseline (n = 28) | 1144.32 ± 185.87 | 463.54 ± 107.72 |
| 3 wk (n + 13) | 1343.31 ± 229.30 | 581.62 ± 140.16 |
| GROUP 2 (SHAM) | | |
| Baseline (n = 7) | 1027.71 ± 106.47 | 395.86 ± 54.73 |
| 3 wk (n = 7) | 1069.29 ± 145.91 | 443.50 ± 45.18 |

Figure 3:
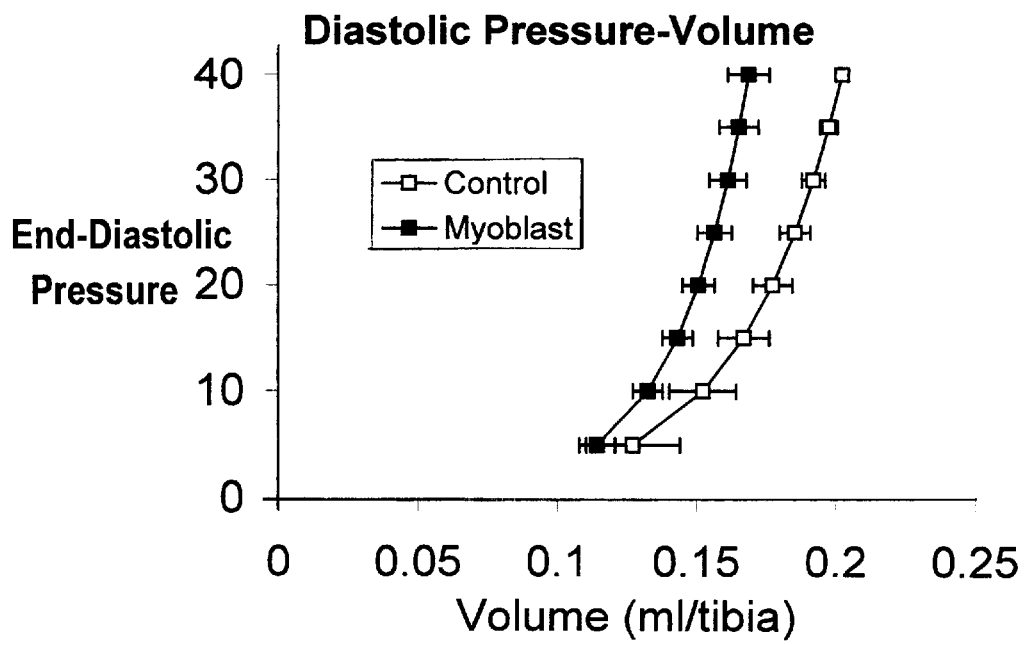
FIGS. 3–4 show that transplanted animals (myoblast and fibroblast) showed improvements in diastolic pressure-volume as compared to nontransplanted control animals.
Figure 4:
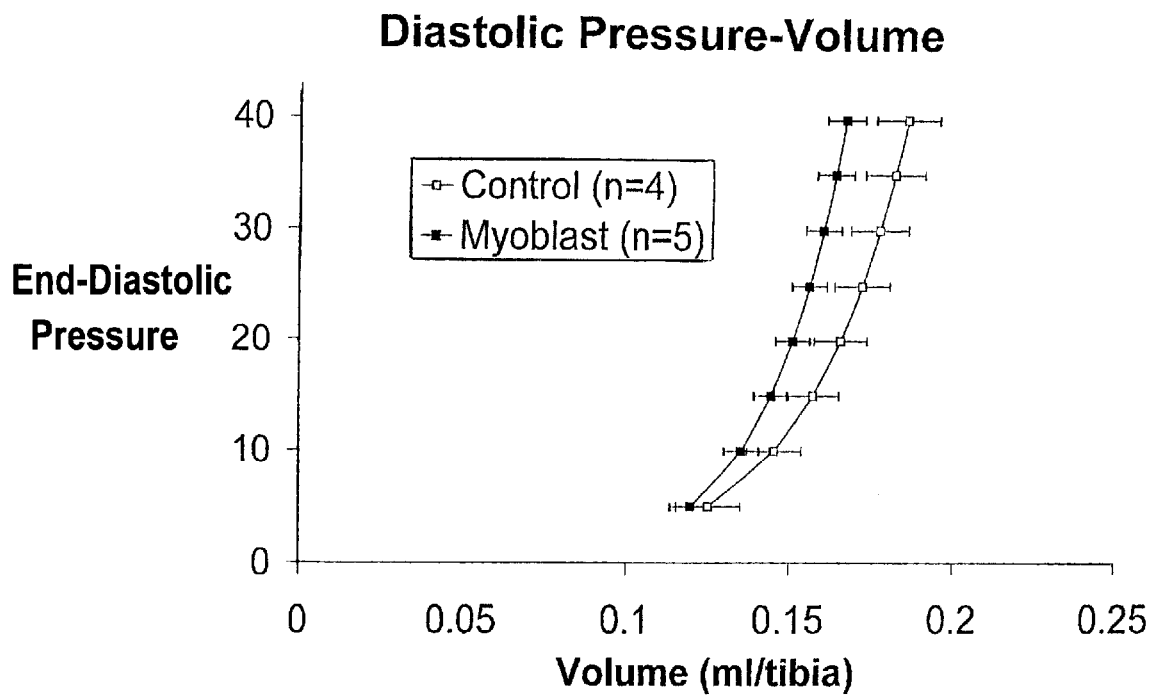

In addition, FIGS. 3 and 4 show that transplanted animals (myoblast) showed improvements in diastolic pressure-volume as compared to nontransplanted control animals. FIGS. 3 and 4 show a reduction in the end-diastolic pressure to volume (corrected for animal size) ratio. These data indicate that the left ventricle of the animals transplanted with myoblasts is being strengthened so that the volume of red blood cells in transplanted hearts is smaller as pressure is increased.

Example 6

Comparison of Transplantation Results on Ventricular Remodeling and Contractile Function After Myocardial Infarction The following transplantations of cells into male Lewis rats were performed. In this example, subjects were given experimentally induced myocardial infarctions by coronary ligation on day 1 (see Pfeffer et al. (1979) Circ. Res. 44:503–512; Jain et al. (2000) Cardiovasc. Res. 46:66–72; Eberli et al. (1998) J. Mol. Cell. Cardiol. 30:1443–1447). Animals were allowed to recover for one week. Transplantation was performed after the one week resting period. Myoblasts and fibroblasts isolated from skeletal hind leg muscle of neonatal Lewis rats were isolated and grown on laminin in growth media supplemented with 20% fetal bovine serum for 48 hours. Cells were resuspended in HBSS at $10^7$ cells/mL, and $10^6$ cells/heart were injected (6 to 10 injections) as follows:

(control): non-infarcted control (MI): myocardial infarction+sham injection (MI+): myocardial infarction+cell injection Three groups of animals were studied at three and six weeks following cell therapy.

Figure 5A:
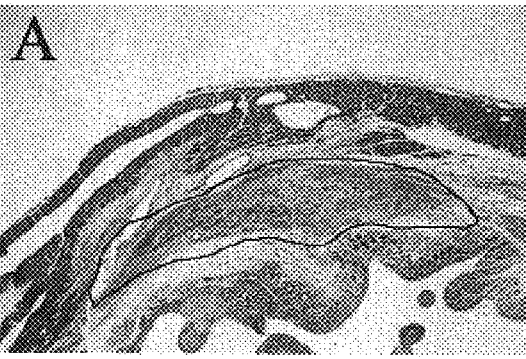
FIGS. 5A–5F show myoblast survival in infarcted myocardium at 9 days post-implantation.
Figure 5D:
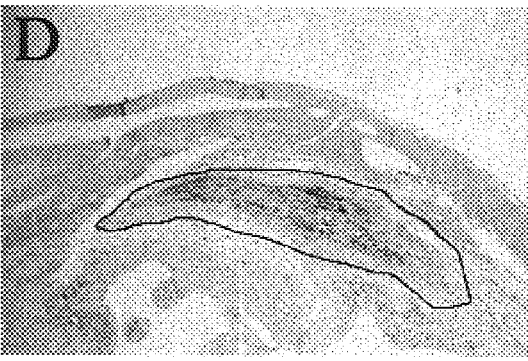
Figure 5B:
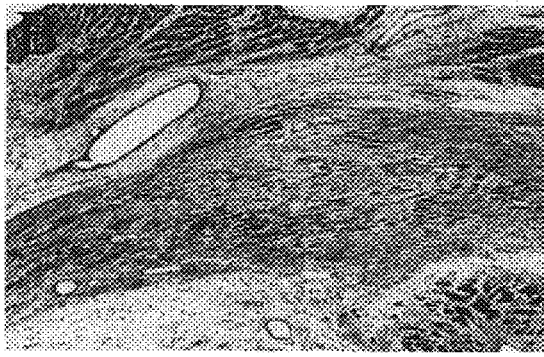
Figure 5E:
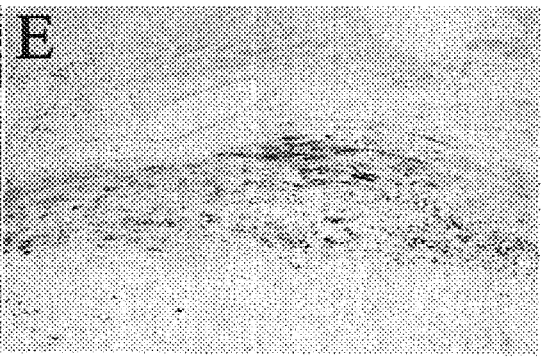
Figure 5C:
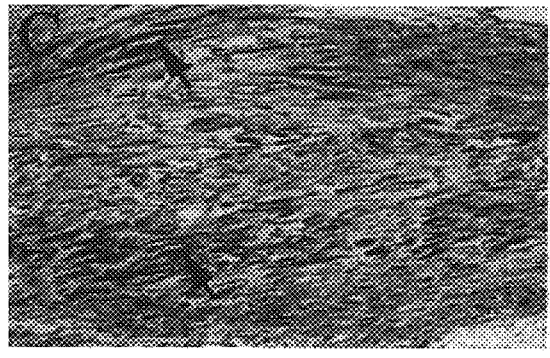
Figure 5F:
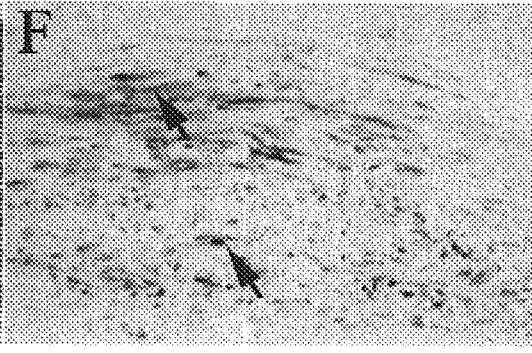

Graft survival was assessed by trichome staining and immunocytochemistry for detection of skeletal myoblasts (anti-myogen stain) and mature myoblasts (anti-skeletal myosin stain). Graft survival was verified at 9 days (FIG. 5) following myoblast implantation. Myogenin positive staining was observed as early as 9 days post-implantation (FIGS. 5D–F), while skeletal myosin heavy chain expression was not observed until three weeks post-implantation. Myoblast survival was confirmed in 6 of 7 and in 9 of 9 animals at three and six weeks post-therapy, respectively. Animals undergoing syngenic cell therapy displayed no evidence for cell rejection, as determined by weight loss, additional mortality or macrophage accumulation in tissue sections.

Figure 6:
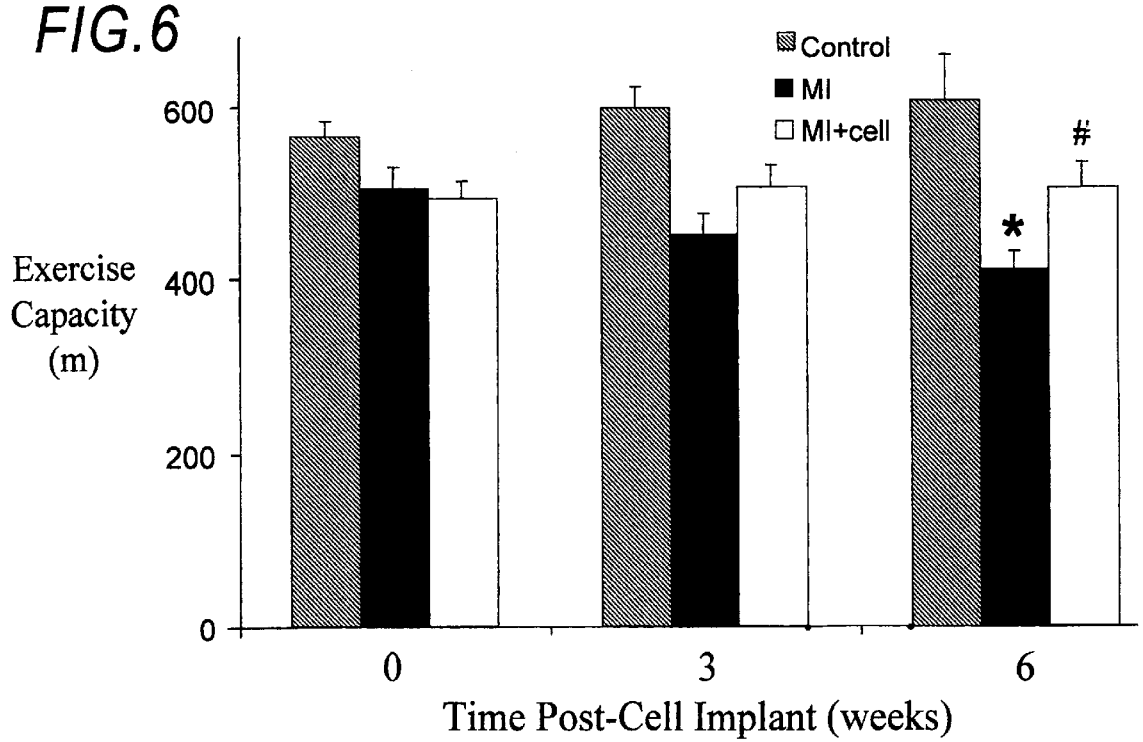
FIG. 6 shows that transplanted post-myocardial infarction animals (myoblast and fibroblast) showed improvements in systolic pressure-volume as compared to nontransplanted control animals.

Maximum exercise capacity, a measure of in vivo ventricular function and overall cardiac performance, was determined in all animals prior to cellular implantation (one week post-MI), as well as three and six weeks post-therapy (FIG. 6). MI animals exhibited a gradual decline in exercise performance with time, showing a greater than 30 percent reduction in exercise capacity relative to control animals at six weeks. Cell therapy (MI+) prevented the continued decline of post-MI exercise capacity, suggesting a protection against the progressive deterioration of in vivo cardiac function.

Figure 7A:
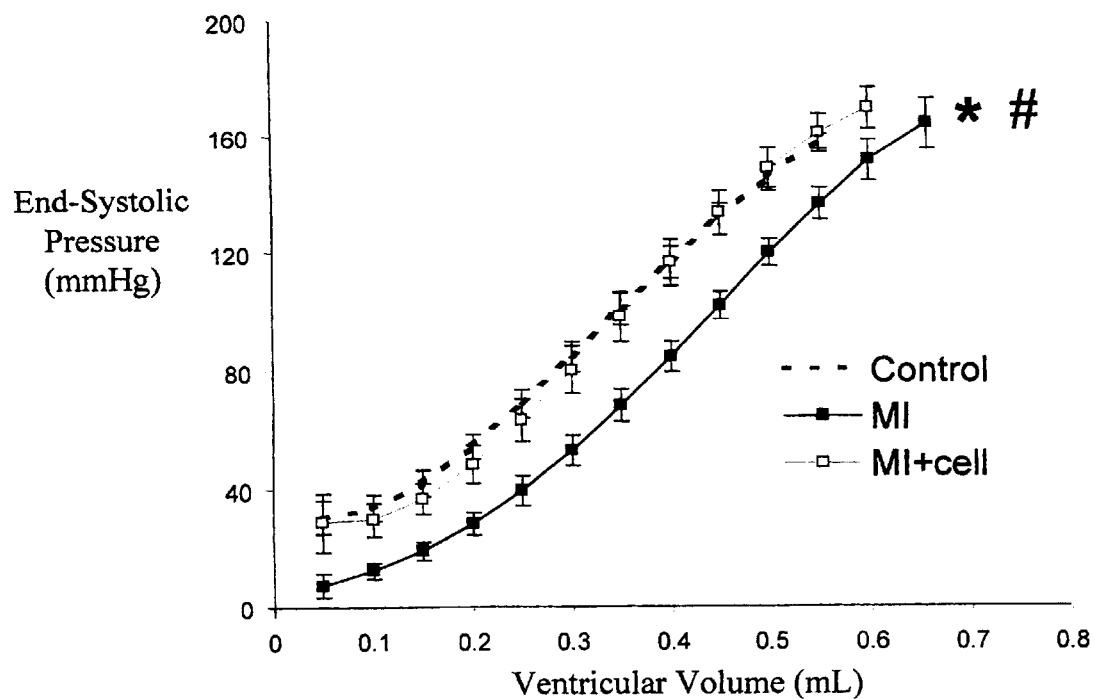
FIGS. 7A–7B show that transplanted post-myocardial infarction animals (myoblast and fibroblast) showed improvements in diastolic pressure-volume as compared to nontransplanted control animals.
Figure 7B:
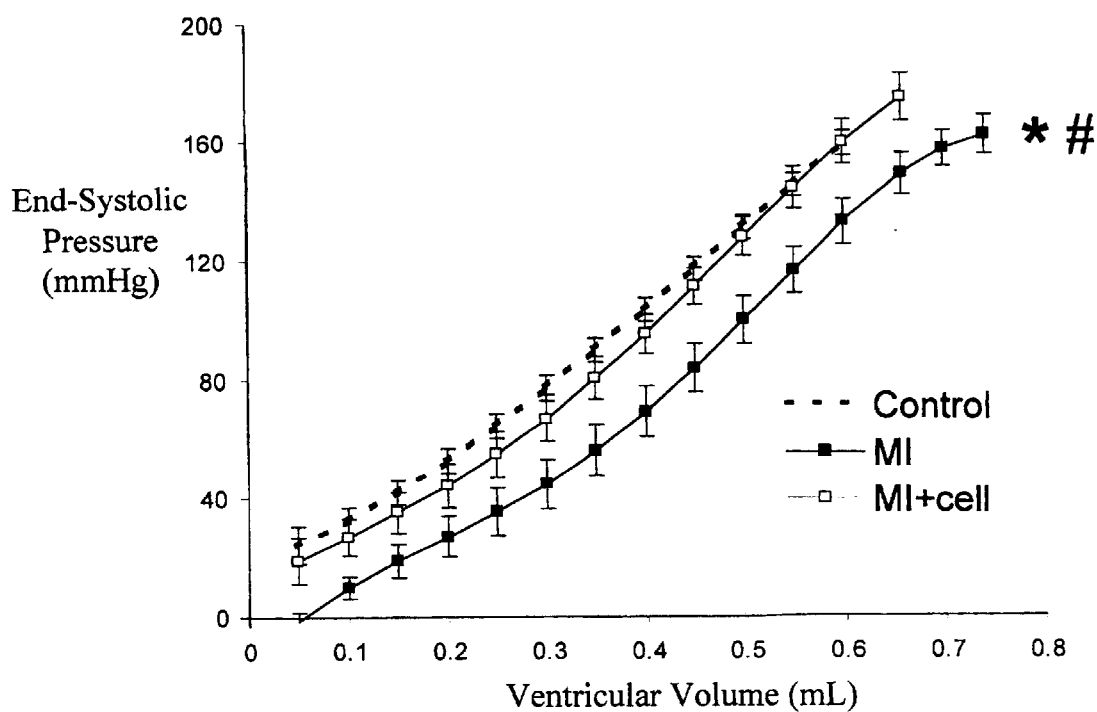

Cardiac contractile function, measured using systolic pressure-volume curves, was assayed by whole heart Langendorff perfusion studies in isolated isovolumically beating hearts (as described in Jain et al. (2000) Cardiovasc. Res. 46:66–72; Eberli et al. (1998) J. Mol. Cell. Cardiol. 30:1443–1447) (FIG. 7). Non-infarcted control hearts exhibited a typical rise in systolic pressure with increasing ventricular volume. Three weeks post-implantation, MI hearts displayed a rightward shift in the systolic pressure-volume curve (FIG. 7A). Cell implantation prevented this shift in MI+ hearts, resulting in greater systolic pressure generation at any given preload (ventricular volume). There was, however, no significant difference in the peak systolic pressure generated at maximum ventricular volume (at an end diastolic pressure of 40 mmHG) among groups. The beneficial effects of cell therapy were also observed at six weeks post-therapy (FIG. 7B), suggesting an improvement of ex-vivo global contractile function with myoblast implantation.

Figure 8A:
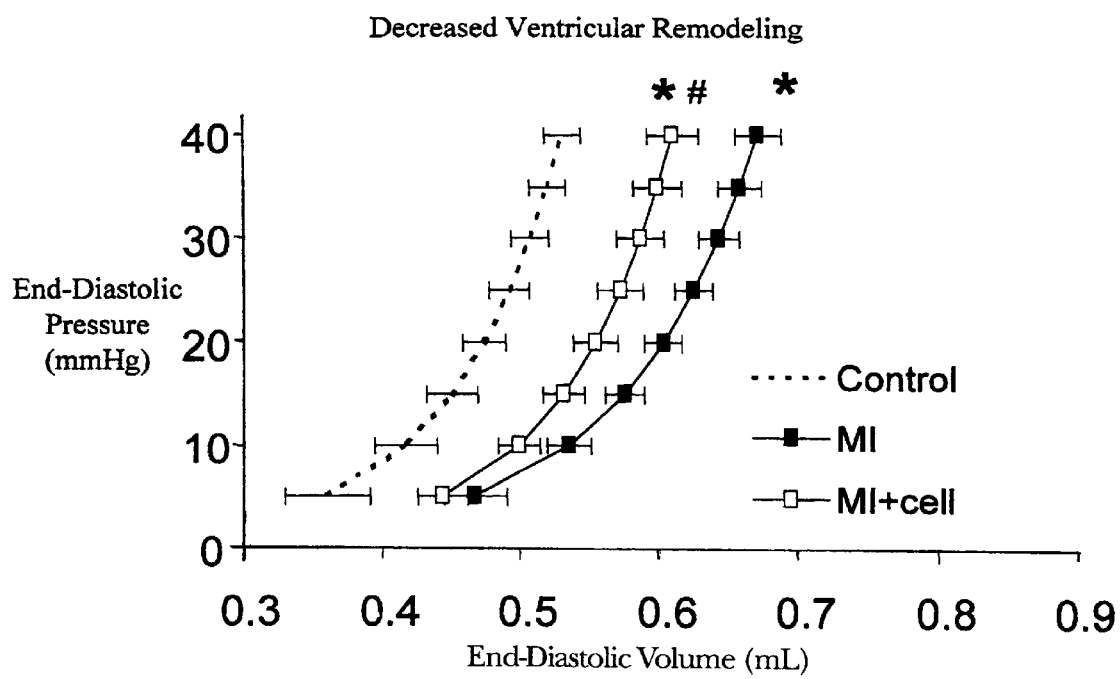
FIGS. 8A–8B show that transplanted post-myocardial infarction animals (myoblast and fibroblast) show no significant decrease in infarct wall thickness as compared to nontransplanted control animals.
Figure 8B:
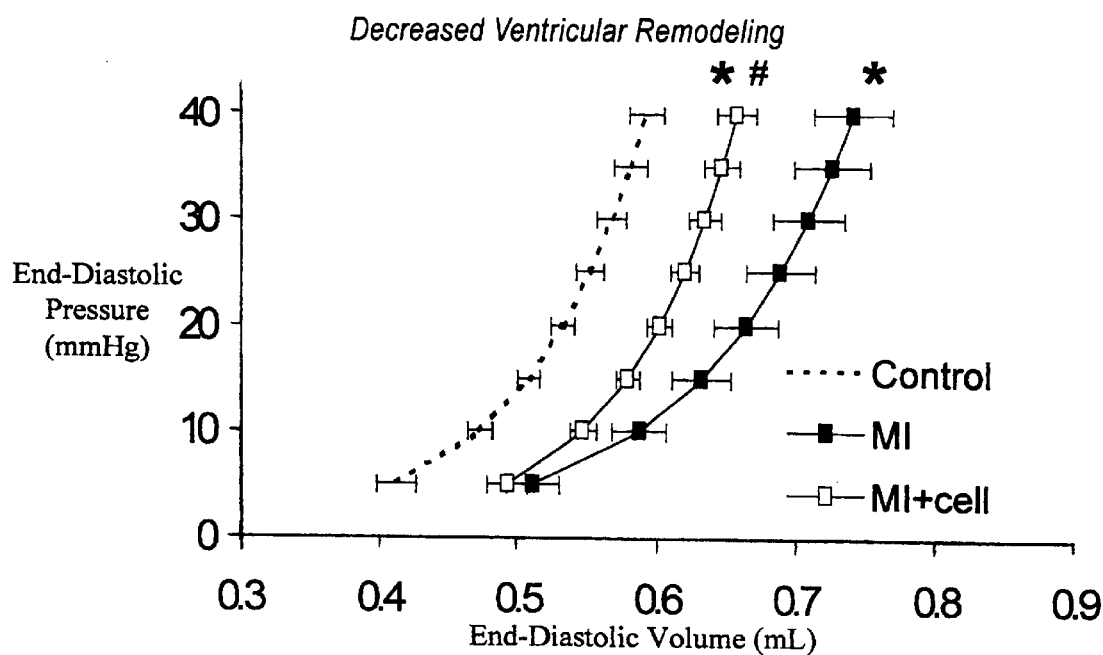

In addition to pump dysfunction, ventricular remodeling characteristically results in progressive global cavity enlargement. Ventricular dilation was assessed with diastolic pressure-volume relationships, established in isolated hearts through monitoring of distending pressures over a range of diastolic volumes (as described in Jain et al.; Eberli et al., supra) (FIG. 8). At all time points, MI hearts exhibited substantially enlarged left ventricles relative to non-infarcted control hearts at any given distending pressure, demonstrated by a rightward repositioning of the pressure-volume curve. Cell therapy, however, caused a significant reduction in ventricular cavity dilation, placing hearts from the MI+ group significantly leftward of MI group at both three and six weeks post-implantation, suggesting an attenuation of deleterious post-myocardial infarction ventricular remodeling with cell implantation.

Ventricular remodeling was further investigated through morphometric analysis of tissue sections. At all time points, MI and MI+ hearts exhibited enlarged chamber diameters compared to non-infarcted control hearts. Six weeks following cell therapy, hearts from the MI+ group had a reduced endocardial cavity diameter relative to MI hearts, suggesting an attenuation of ventricular dilation, similar as observed with diastolic pressure-volume curves in FIG. 8B. In addition, MI hearts exhibited a decrease in infarct wall thickness at both three and six weeks post-therapy, suggesting characteristic post-myocardial infarction scar thinning and infarct expansion. MI+ hearts, however, had no significant reduction in infarct wall thickness relative to non-infarcted control hearts. Septal wall thickness was comparable among all groups at both three and six weeks post-therapy. These data indicate that myoblast implantation following MI improves both in vivo and ex vivo indices of global ventricular dysfunction and deleterious remodeling and suggests cellular implantation may be beneficial post-MI.

Example 7

Autologous Myoblast and Fibroblast Transplantation for the Treatment of End-Stage Heart Disease Autologous myoblasts and fibroblasts derived from skeletal muscle are transplanted into the myocardium of subjects in end stage heart failure. The human subjects in the study are candidates for heart transplant surgery and are scheduled for placement of a left ventricular assist device as a bridge to orthotopic transplantation.

Prior to transplant, myoblasts and fibroblasts are expanded in vitro from satellite cells obtained from a biopsy of the subject's skeletal muscle. The composition of the cells is preferably 40–60% myoblasts. The cells, at a concentration of $8 \times 10^7$ cells per ml, are injected into the peri-infarct zone of the left ventricle. Injections of up to 100 μl are made into up to 35 sites, with a maximum of $300 \times 10^6$ cells injected.

The safety of myoblast and fibroblast transplantation is assayed based upon unexpected adverse effects, such as abnormal cardiac function. Preliminary information on the autologous graft survival and the potential for improvement of cardiac function that might be associated with the autologous myoblast and fibroblast transplantation is obtained.

Example 8

Autologous Myoblast and Fibroblast Transplantation for the Treatment of Infarcted Myocardium Autologous myoblasts and fibroblasts derived from skeletal muscle are transplanted into and around the ischemic or scarred areas of the myocardium, post myocardial infarction. The human subjects in the study have a myocardial infarction and have additional cardiac disease consisting of left ventricular dysfunction that places the subject in the high risk group of candidates for coronary artery bypass graft.

Prior to transplant, myoblasts and fibroblasts are expanded in vitro from satellite cells obtained from a biopsy of the subject's skeletal muscle. The composition of the cells is preferably 40–60% myoblasts. The cells, at a concentration of $8 \times 10^7$ cells per ml, are injected into and around the infarct site in a region of the wall of the left ventricle that has adequate perfusion. Injections of up to 100 μl are made into up to 30 sites.

The safety of myoblast and fibroblast transplantation is assayed based upon adverse events due the transplanted cells and the transplantation procedure. Echocardiography and magnetic resonance imaging are used to evaluate regional wall motion, an assay to detect improvement of cardiac function.

Equivalents

Those skilled in the art will recognize, or be able to ascertain using no more than routine experimentation, many equivalents of the specific embodiments of the invention described herein. Such equivalents are intended to be encompassed by the following claims.

References

Apstein, C. S., O. H. Bing, and H. J. Levine. 1976. Cardiac muscle function during and after hypoxia: effects of glucose concentration, mannitol and isoproternol. *J Mol Cell Cardiol*. 8:627.

Baily, R. G., J. C. Lehman, S. S. Gubin, and T. I. Musch. 1993. Non-invasive assessment of ventricular damage in rats with myocardial infarction. *Cardiovasc Res*. 27:851.

Blau, Helen and Hughes, Simon. Publication Date: 1990. International Publication No. WO 90/15863. (International Application No. PCT/US90/03352).

Chen G. and Quinn L. S. 1992. Partial characterization of skeletal myoblast mitogens in mouse crushed muscle extract. *J. Cell Physiol*. 153(3):563–74.

Connelly, C. M., S. Ngoy, F. J. Schoen, and C. S. Apstein. 1992. Biomechanical properties of reperfused transmural myocardial infarcts in rabbits during the first week after infarction. Implications for left ventricular rupture. *Circ Res*. 71:401.

Desai et al. 1997. Cardiovascular Indexes in the Mouse at Rest and with Exercise: New Tools to Study Models of Cardiac Disease. *Am. J. Physiol*. 272:H 1053–1061.

Desai et al. 1999. Phospholamban Deficiency Does Not Compromise Exercise Capacity. *Am. J. Physiol*. 276:H1 172–177.

Eberli, F. R., F. Sam, S. Ngoy, C. S. Apstein, and W. S. Colucci. 1998. Left-ventricular structural and functional remodeling in the mouse after myocardial infarction: assessment with the isovolumetrically-contracting Langendorff heart. *J Mol Cell Cardiol*. 30: 1443.

Fewell et al. 1997. A Treadmill Exercise Regimen for Identifying Cardiovascular phenotypes in Transgenic Mice. *Am. J. Physiol*. 273:H1 595–605.

Field, L. J. 1997. Non-Human Mammal Having a Graft and Methods of Delivering Protein to Myocardial Tissue. U.S. Pat. No. 5,602,301 (filed Nov. 16, 1994).

Field, L. J. et al. Publication Date: 1995. International Publication No. WO 95/14079. (International Application No. PCT/US94/13141).

Jain, M. et al. 2000. Angiotensin II Receptor Blockade Attenuates the Deleterious Effects of Exercise Training on Post-MI Ventricular Remodelling in Rats. *Cardiovasc. Res*. 46:66–72. Koh, G. Y. et al. 1993 Differentiation and Long-Term Survival of C2C12 Myoblast Grafts in Heart. *J. Clin. Invest*. 92:1548–1554.

Law, P. K. and Goodwin, T. G. 1992. Compositions for and Methods of Treating Muscle Degeneration and Weakness. U.S. Pat. No. 5,130,141 (filed May 30, 1991).

Li, R. K. et al. 1998. Cell therapy to repair broken hearts. *Can J Cardiol*; 14(5):735–744.

Li, R. K. et al. 1996. Human pediatric and adult ventricular cardiomyocytes in culture: assessment of phenotypic changes with passaging. *Cardiovascular Research*. 32:362–373.

Li, R. K. et al. 1997. Natural History of Fetal Rat Cardiomyocytes Transplanted Into Adult Rat Myocardial Scar Tissue. *Circulation*. 96(9):II-179–II-187.

Mannion, J. D. et al 1986. Histochemical and Fatigue Characteristics of Conditioned Canine Latissimus Dorsi Muscle. *Circulation Research*. 58(1):298–304.

Morrow, N. G. et al 1990. Increased Expression of Fibroblast Growth Factors in a Rabbit Skeletal Muscle Model of Exercise Conditioning. *J. Clin. Invest*. 85:1816–1820.

Murry, C. E. et al 1996. Skeletal Myoblast Transplantation for Repair of Myocardial Necrosis. *J. Clin. Invest*. 98(11):2512–2523.

Pfeffer et al 1979. Myocardial Infarct Size and Function in Rats. *Circ. Res*. 44:503–512.

Pfeffer, P. F., and E. Thorsby. 1982. HLA-restricted cytotoxicity against male-specific (HY) antigen after acute rejection of an HLA-identical sibling kidney: clonal distribution of the cytotoxic cells. *Transplantation*. 33:52.

Robinson, S. W. et al. 1996. Arterial Delivery of Genetically Labelled Skeletal Myoblasts to the Murine Heart: Long-Term Survival and Phenotype Modification of Implanted Myoblasts. *Cell Transplantation*. 5(1):77–91.

Schweitzer, J. S. et al 1987. Fibroblasts Modulate Expression of Thy-1 on the Surface of Skeletal Myoblasts. *Experimental Cell Research*. 172:1–20.

Taylor, D. A. et al. 1997. Delivery of Primary Autologous Skeletal Myoblasts into Rabbit Heart by Coronary Infusion: A Potential Approach to Myocardial Repair. *Proceedings of the Association of American Physicians*. 109 (3):245–253.

Taylor, D. A. et al. 1998. Regenerating functional myocardium: Improved performance after skeletal myoblast transplantation. *Nature Medicine*. 4(8):929–933.

Trueblood et al. 1999. Relationship Between Exercise Intolerance and Myocardial Remodeling Post-MI in the Rat. *Circulation*. 100:1–55. Abstract.

Zelenika, D., E. Adams, A. Mellor, E. Simpson, P. Chandler, B. Stockinger, H. Waldmann, and S. P. Cobbold. 1998. Rejection of H-Y disparate skin grafts by monospecific CD4+ Th1 and Th2 cells: no requirement for CD8+ T cells or B cells. *J. Immunol.* 161: 1868.

What is claimed is:

1. A composition comprising:

isolated skeletal myoblasts; and isolated fibroblast cells, the composition being substantially free of myotubes.

2. The composition of claim 1, which composition comprises at least 5% fibroblasts.

3. The composition of claim 1 or claim 2, comprising:

isolated human skeletal myoblasts; and isolated human fibroblasts, the composition being substantially free of myotubes.

4. The composition of claim 1 or claim 2, wherein the composition is cultured in vitro for at least 7 days.

5. The composition of claim 1 or claim 2, which composition comprises cells that have been cultured in vitro for fewer than 20 population doublings.

* * * * *

US006673604C1

(12) INTER PARTES REEXAMINATION CERTIFICATE (0054th)

United States Patent
Edge

(10) Number: US 6,673,604 C1
(45) Certificate Issued: Mar. 24, 2009

(54) MUSCLE CELLS AND THEIR USE IN CARDIAC REPAIR

(75) Inventor: Albert Edge, Cambridge, MA (US)

(73) Assignee: Genvec, Inc., Gaithersburg, MD (US)

Reexamination Request:
No. 95/000,152, May 10, 2006

Reexamination Certificate for:
Patent No.: 6,673,604
Issued: Jan. 6, 2004
Appl. No.: 09/624,885
Filed: Jul. 24, 2000

Related U.S. Application Data
(60) Provisional application No. 60/145,849, filed on Jul. 23, 1999.

(51) Int. Cl.
*C12N 5/06* (2006.01)
*C12N 5/08* (2006.01)

(52) U.S. Cl. .................. 435/347; 435/325; 435/371; 424/93.21

(58) Field of Classification Search ................. None
See application file for complete search history.

(56) References Cited

U.S. PATENT DOCUMENTS

| | | | |
|---|---|---|---|
| 6,099,832 | A | 8/2000 | Mickle et al. |
| 7,189,391 | B2 | 3/2007 | Tremblay |
| 2007/0178077 | A1 | 8/2007 | Tremblay |

FOREIGN PATENT DOCUMENTS

| | | |
|---|---|---|
| EP | 00946713 | 3/2007 |
| WO | WO-2004/014302 | 2/2004 |

OTHER PUBLICATIONS

Moore, et al., *The Developing Human, Clinically Oriented Embryology*, 6th edition, W.B. Saunders Company, 1998, p. 8.

Hagoege, et al., "Skeletal myoblast transplantation in ischemic heart failure: long–term follow–up of the first phast I cohort of patients", *Circulation*, 114(Suppl. 1): 1108–13, Jul. 4, 2006.

Lafreniere, et al., "Growth factors improve the in vivo migration of human skeletal myoblasts by modulating their endogenous proteolytic activity", *Transplantation*, 77(11): 1741–7, Jun. 15, 2004.

Lafreniere, et al., "Interleukin–4 improves the migration of human myogenic precursor cells in vitro and in vivo", *Experimental Cell Research*, 312(7): 1127–41, Apr. 15, 2006.

Menaschoe, et al., "Autologous skeletal myoblast transplantation for severe postinfarction left ventricular dysfunction", *J. Am Coll Cardiol*, 41(7): 1078–83, Apr. 2, 2003.

Messas, et al., "Autologous myoblast transplantation for chronic ischemic mitral regurgitation", *J. Am Coll Cardiol*, 47(10): 2086–93 May 16, 2006.

Messas, et al., "Chordal cutting does not adversely affect left ventricle contractile function", *Circulation*, 114(1Suppl): 1521–8, Jul. 4, 2006.

Allanore, et al., "Effects of Corticosteroids And Immunosuppressors On Idiopathic Inflammatory Myopathies–related Myocarditis evaluated By Magnetic Resonance Imaging," *Annals of the Rheumatic Diseases*, 64: 74–75, 2005.

Benabdallah, et al., "Improved Success Of Myoblast Transplantation In *mdx* Mice By Blocking The Myostatin Signal," *Transplantation*, 79: 1696–1702, 2005.

Bouchentouf, et al., "Real–time Imaging Of Myoblast Transplantation Using The Human Sodium Iodide Symporter," *Bio Techn.*, 38: 937–942, 2005.

Brasselet, et al., "Skeletal Myoblast Transplantation Through A Catheter–Based Coronary Sinus Approach: An Effective Means Of Improving Function Of Infarcted Myocardium," *Europ. Heart Journal*, 26; 1551–1556, 2005.

Bujold, et al., "Autotransplantation In Mdx Mice of Mdx Myoblasts Genetically Corrected By An HSV–1 Amplicon Vector," *Cell Transplant*, 11: 759–767, 2002.

Camirand, et al., "Novel Duchenne Muscular Dystrophy Treatment Through Myoblast Transplantation Tolerance With Anti–CD45RB, Anti–CD154 And Mixed Chimerism," *Am J. Transplant*, 4: 1255–1265, 2004.

Campeau, et al., "Transfection Of Large Plasmids In Primary Human Myoblasts," *Gene Ther.*, B: 1387–1394, 2001.

Desnuelle, et al., "The Possible Place Of Autologus Cell Therapy In Facioscapulohumeral Muscular Dystrophy," *Bull Acad. Natl. Med.*, 189: 697–714, 2005. (Abstract only).

Drouin, et al., "Adult Muscle–derived Stem Cells Culture," *Abstracts of Papers Am. Chem. Soc.*, 229: U200, 2005.

Duboc, et al., "Effect Of Perindopril On The Onset and Progression Of Left Ventricular Dysfunction In Duchenne Muscular Dystrophy," *J. Am. Coll. Cardiol.*, 45: 855–857, 2005.

El Fahime, et al., "In Vivo Migration Of Transplanted Myoblasts Requires Matrix Metalloproteinase Activity," *Exp. Cell. Res.*, 258: 279–287, 2000.

Fromes, et al., "Gene Delivery To The Myocardium By Intrapericardial Injection," *Gene Ther.*, 6: 683–688, 1999.

Guoerette, et al., "Efficient Myoblast Transplantation In Mice Immunosuppressed With Monoclonal Antibodies And CTLA4 Ig," *Transplant Proc.*, 29: 1932–1934, 1997.

Guoerette, et al., "Immunosuppression With Monoclonal Antibodies And CTLA4–lg After Myoblast Transplantation In Mice," *Transplantation*, 62: 962–967, 1996.

Hagoege, A.A, et al., "Viability And Differentiation Of Autologous Skeletal Myoblast Grafts In Ischaemic Cardiomyopathy.", *The Lancet* 361: 491–492, 2003.

(Continued)

*Primary Examiner*—Padmashri Ponnaluri

(57) ABSTRACT

Muscle cells and methods for using the muscle cells are provided. In one embodiment, the invention provides transplantable skeletal muscle cell compositions and their methods of use. In one embodiment, the muscle cells can be transplanted into patients having disorders characterized by insufficient cardiac function, e.g., congestive heart failure, in a subject by administering the skeletal myoblasts to the subject. The muscle cells can be autologous, allogeneic, or xenogeneic to the recipient.

OTHER PUBLICATIONS

Leobon, et al., "Evidence For In Vivo Coupling Between Transplanted Embryonic Stem Cells And Host Cardiomyocytes," *Circulation*, 112: U146, 2005.

Leor, et al., Transplantation of Fetal Myocardial Tissue into the Infarcted Myocardium of Rat, A Potential Method for Repair of Infarcted Myocardium, *Circulation*, 94:(Supplement II), II–332–II336, 1996.

Maurel, et al., "Patterns Of Cell Death And Proliferation After Skeletal Myoblast Transplantation,"*Europ. Heart Journal*, 25: 265, 2004.

Maurel, et al., "Can Cold Or Heat Shock Improve Skeletal Myoblast Engraftment In Infarcted Myocardium?" *Transplantation*, 80: 660–665, 2005.

Menasche, "Cardiac Myoblasts," *Ernst Schering Res. Foundation Workshop*, 21–34, 2005.

Menasche, et al., "Cell Transplantation in Myocardium", *Ann Thorac Surg*, 75: S20–S28, 2003.

Menasche, "Role Of Stem Cells In Cardiac Repair," *Bull Acad. Natl. Med.*, 189: 615–624, 2005. (Abstract only).

Menasche, "Stem Cells For Clincal Use In Cardiovascular Medicine—Current Limitations And Future Perspectives," *Thrombosis and Haemostasis*, 94: 697–701, 2005.

Meune, et al., "Cardiac Involvement In Female Carriers Of Duchenne And Becker Muscular Dystrophy," *Circulation*, 110: 362, 2004.

Meune and Duboc, "Can Perindopril Delay The Onset Of Heart Failure In Duchenne Muscular Dystrophy?" *J. of Am. College of Cardiology*, 46: 1782, 2005.

Moisset, et al., "Expression Of Human Dystrophin Following The Transplantation Of Genetically Modified mdx Myoblasts," *Gene Ther.*, 5: 1340–1346, 1998.

Moisset, et al., "Successful Transplantation Of Genetically Corrected DMD Myoblasts Following Ex Vivo Transduction With The Dystropin Minigene," *Biochem Biophys Res. Commun.*, 247: 94–99, 1998.

Muchir, et al., "Nuclear Envelope Alterations In Fibroblasts From Patients With Muscular Dystrophy, Cardiomyopathy, And Partial Lipodystrophy Carrying Lamin A/C Gene Mutations," *Muscle &Nerve*, 30: 444–450, 2004.

Murry, et al., "Cell–Based Cardiac Repair," *Circulation*, 112:3174–3183, 2005.

Pitard, et al., "A Nonionic Amphiphile Agent Promotes Gene Delivery In Vivo To Skeletal And Cardiac Muscles," *Hum. Gene Ther.*, 13: 1767–1775, 2002.

Quenneville, et al., "Nucleofection Of Muscle–Derived Stem Cells And Myoblasts With phiC31 Integrase: Stable Expression Of A Full–length–dystrophin Fusion Gene By Human Myoblasts," *Mol. Ther.*, 10: 679–687, 2004.

Schwartz and Mercadier, "Molecular And Cellular Biology Of Heart Failure," *Curr. Opin. Cardiol.*, 11: 227–236, 1996.

Skuk, et al., "Dystrophin Expression In Muscles Of Duchenne Muscular Dystrophy Patients After High–density Injections Of Normal Myogenic Cells," *J. Neuropathol Exp. Neurol.*, 65: 371–386, 2006.

Skuk, et al., "Experimental And Therapeutic Approaches To Muscular Dystrophies," *Curr. Opin. Neurol.*, 15: 563–569, 2002.

Torrente, et al., "Identification Of A Putative Pathway For The Muscle Homing Of Stem Cells In A Muscular Dystrophy Model," *J. Cell Biol.*, 162: 511–520, 2003.

Vilquin, "Myoblast Transplantation: Clinical Trials And Perspectives," *Acta Myol.*, 24: 119–127, 2005.

Vilquin, et al., "Normal Growth And Regenerating Ability Of Myoblasts From Unaffected Muscles Of Facioscapulohumeral Muscular Dystrophy Patients," *Gene Therapy*, 12: 1651–1662, 2005.

Camirand, et al., *Am. J. Transplant*, 4(8):1255–1265, 2004.

Coirault, et al., *Circulation*, 114(18, Suppl. S):198, 2006.

Menasche, et al., *Circulation*, 114(22):2426, 2006.

Menasche, *Progress in Cardiovascular Diseases*, 50(1):7–17, 2007.

Mills, et al., *Exp. Cell. Res.*, 313(3):527–537, 2007.

Peault, et al., *Mol. Ther.*, 15(5):867–877, 2007.

Retuerto, et al., *J. Thorac. Cardiovasc. Surg.*, 133(2):478–484, 2007.

Siepe, et al., *Artificial Organs*, 31(6):425–433, 2007.

Skuk, et al., *J. of Neuropathology &Experimental Neurology*, 65(4):371–386, 2006.

Skuk, et al., *Transplantation*, 84(10):1307–1315, 2007.

Stephan, et al., *Cell Transplantation*, 16(3):391–402, 2007.

Vilquin, et al., *Med. Sci. (Paris)*, 20(6–7):651–652, 2004.

Allen, R.E., et al., "Regulation of skeletal muscle satellite cell proliferation and differentiaion by transforming growth factor–beta, insulin–like growth fctor I, and fibroblast growth factor", J. Cell Physiol., (1989), 138(2):311–5.

Allen, R.E., et al., "Desmin is Present in Proliferating Rat Muscle Satellite Cells but Not in Bovine Muscle Satellite Cells", J. Cell. Physiol., (1991), 149:525–535.

Jong, H.J., et al., "Study of myoblast culture and myoblast transfer therapy in dystrophic mice", Kaohsiung J. Med Sci., (1995) Jul.;11(7):398–408.

Kinoshita, I., et al., "Pretreatment of myoblast cultures with basic fibroblast growth factor increases the efficacy of their transplantation in mdx mice", Muscle & Nerve. (1995) Aug.;18 (8):834–41.

Cohen, R., et al., "Effect of a tumor promoter on myogenesis", Nature, (1977), 266(7); 538–540.

Rando, T.A., et al., "Primary mouse myoblast purification, characterization, and transplantation for cell–mediated gene therapy", J. Cell. Biol. (1994) Jun.;125(6):1275–87.

Shainberg, A., et al., "Control of myogenesis in vitro by $Ca^{2+}$ concentration in nutritional medium", Exptl. Cell Res. (1969) Nov.;58(1):163–7.

Webster, C., et al., "Isolation of human myoblasts with the fluorescence–activated cell sorter", Exptl. Cell Res. (1988) Jan.;174(1):252–65.

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1–5 are cancelled.

\* \* \* \* \*